(12) United States Patent
Schreiter et al.

(10) Patent No.: US 9,518,996 B2
(45) Date of Patent: Dec. 13, 2016

(54) FLUORESCENT PROTEIN-BASED CALCIUM INTEGRATORS

(71) Applicant: Howard Hughes Medical Institute, Chevy Chase, MD (US)

(72) Inventors: Eric R. Schreiter, Ashburn, VA (US); Loren L. Looger, Sterling, VA (US); Benjamin F. Fosque, Arlington, VA (US)

(73) Assignee: Howard Hughes Medical Institute, Chevy Chase, MD (US)

(*) Notice: Subject to any disclaimer, the term of this patent is extended or adjusted under 35 U.S.C. 154(b) by 0 days.

(21) Appl. No.: 14/452,428

(22) Filed: Aug. 5, 2014

(65) Prior Publication Data
US 2015/0037812 A1    Feb. 5, 2015

Related U.S. Application Data

(60) Provisional application No. 61/862,436, filed on Aug. 5, 2013.

(51) Int. Cl.
| | |
|---|---|
| *G01N 33/84* | (2006.01) |
| *G01N 33/58* | (2006.01) |
| *C07K 14/47* | (2006.01) |
| *C12N 9/12* | (2006.01) |

(52) U.S. Cl.
CPC .......... *G01N 33/84* (2013.01); *C07K 14/4728* (2013.01); *C12N 9/12* (2013.01); *G01N 33/582* (2013.01); *C07K 2319/095* (2013.01); *C07K 2319/21* (2013.01); *C07K 2319/60* (2013.01)

(58) Field of Classification Search
None
See application file for complete search history.

(56) References Cited

PUBLICATIONS

Li et al., Regulation of a nuclear export signal by an adjacent inhibitory sequence: the effector domain of the influenza virus NS1 protein., Proc Natl Acad Sci U S A. (1998), vol. 95(9), pp. 4864-4869.*
B2BUJ3 NS1 Influenza A virus (last viewed on Jan. 12, 2016).*
Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Stites & Harbison, PLLC; Mandy Wilson Decker; Sean P. Ritchie

(57) ABSTRACT

The presently-disclosed subject matter includes fluorescent protein-based indicators for detecting ions, small molecule analytes, or combinations thereof. In some embodiments the indicators include a polypeptide, which itself includes a fluorescent polypeptide, a compound-binding polypeptide, and a polypeptide target of the compound-binding polypeptide. In some embodiments the polypeptide includes an EosFP polypeptide, a calmodulin polypeptide, and a M13 polypeptide, or fragments and/or variants thereof. The presently-disclosed subject matter also includes methods for detecting calcium in a sample with embodiments of the present polypeptides. In some embodiments the present indicators experience a permanent shift from green to red fluorescent when exposed to an detecting substance, such as calcium.

21 Claims, 23 Drawing Sheets

(56) References Cited

PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*
Wacey et al., Disentangling the perturbational effects of amino acid substitutions in the DNA-binding domain of p53., Hum Genet, 1999, vol. 104, pp. 15-22.*
Branden and Tooze, Introduction to Protein Structure (1999), 2nd edition, Garland Science Publisher, pp. 3-12.*
Miyawaki et al., Fluorescent indicators for Ca2+ based on green fluorescent proteins and calmodulin, Nature (1997), vol. 388(6645), pp. 882-887.*
pRSETB vector (last viewed on Jan. 22, 2016).*
The 3D Structure of GFP (last viewed on Jan. 22, 2016).*
Tian, L., Hires, S.A., Looger, L.L. Imaging neuronal activity with genetically encoded calcium indicators. Cold Spring Harbor protocols 2012, 647-656 (2012).
Guzowski, J.F., Timlin, J.A., Roysam, B., McNaughton, B.L., Worley, P.F., Barnes, C.A. Mapping behaviorally relevant neural circuits with immediate-early gene expression. Current opinion in neurobiology 15, 599-606 (2005).
Tsien, R.Y. Very long-term memories may be stored in the pattern of holes in the perineuronal net. Proc Natl Acad Sci USA 110, 12456-12461 (2013).
O'Connor, D.H., Huber, D., Svoboda, K. Reverse engineering the mouse brain. Nature 461, 923-929 (2009).
Marvin, J.S., Borghuis, B.G., Tian, L., Cichon, J., Harnett, M.T., Akerboom, J., Gordus, A., Renninger, S.L., Chen, T.W., Bargmann, C.I., Orger, M.B., Schreiter, E.R., Demb, J.B., Gan, W.B., Hires, S.A,. Looger, L.L. An optimized fluorescent probe for visualizing glutamate neurotransmission. Nat Methods 10, 162-170 (2013).
Marvin, J.S., Schreiter, E.R., Echevarria, I.M., Looger, L.L. A genetically encoded, high-signal-to-noise maltose sensor. Proteins 79, 3025-3036 (2011).
Alicea, I., Marvin, J.S., Miklos, A.E., Ellington, A.D., Looger, L.L., Schreiter, E.R. Structure of the *Escherichia coli* phosphonate binding protein PhnD and rationally optimized phosphonate biosensors. Journal of molecular biology 414, 356-369 (2011).
Venkatachalam, V., Brinks, D., MacLaurin, D., Hochbaum, D., Kralj, J., Cohen, A.E. Flash memory: photochemical imprinting of neuronal action potentials onto a microbial rhodopsin. Journal of the American Chemical Society 136, 2529-2537 (2014).
Ando, R., Hama, H., Yamamoto-Hino, M., Mizuno, H. & Miyawaki, A. An optical marker based on the Uv-induced green-to-red photoconversion of a fluorescent protein. Proc Natl Acad Sci U S A 99, 12651-12656 (2002).
Baird, G.S., Zacharias, D.A. & Tsien, R.Y. Circular permutation and receptor insertion within green fluorescent proteins. Proc Natl Acad Sci U S A 96, 11241-11246 (1999).
McKinney, S.A., Murphy, C.S., Hazelwood, K.L., Davidson, M.W. & Looger, L.L. A bright and photostable photoconvertible fluorescent protein. Nat Methods 6, 131-133 (2009).
Akerboom, J., Chen, T.W., Wardill, T.J., Tian, L., Marvin, J.S. et al. Optimization of a GCaMP calcium indicator for neural activity imaging. J Neurosci 32, 13819-13840 (2012).
Nienhaus, K., Nienhaus, G.U., Wiedenmann, J., Nar, H. Structural basis for photo-induced protein cleavage and green-to-red conversion of fluorescent protein EosFP. Proc Natl Acad Sci U S A 102, 9156-9159 (2005).
Wardill, T.J., Chen, T.W., Schreiter, E.R., Hasseman, J.P., Tsegaye, G., Fosque, B.F., Behnam, R., Shields, B.C., Ramirez, M., Kimmel, B.E., Kerr, R.A., Jayaraman, V., Looger, L.L., Svoboda, K., Kim, D.S. A neuron-based screening platform for optimizing genetically-encoded calcium indicators. PLoS One 8, e77728 (2013).
Akerboom, J., et al. Genetically encoded calcium indicators for multi-color neural activity imaging and combination with optogenetics. Frontiers in Molecular Neuroscience, vol. 6, Article, 1-29 (2013).
Tian, L., et al. Imaging neural activity in worms, flies and mice with improved GCaMP calcium indicators. Nature Methods, vol. 6, No. 12, 875-884 (2009).
Rodriguez Guilbe, M.M., et al. Crystallization and preliminary X-ray characterization of the genetically encoded fluorescent calcium indicator protein GCaMP2. Acta Cryst. F64, 629-631 (2008).
Hires, S.A., Tian, L., Looger, L.L. Reporting neural activity with genetically encoded calcium indicators. Brain Cell Biology, vol. 36, 69-86 (2008).
Chen, T.W., Wardill, T.J., Sun, Y., Pulver, S.R., Renninger, S. L., Baohan, A., Schreiter, E.R., Kerr, R.A., Orger, M.B., Jayaraman, V., Looger, L.L., Svoboda, K., Kim, D.S. Ultrasensitive fluorescent proteins for imaging neuronal activity. Nature 499, 295-300 (2013).
Akerboom, J., Rivera, J.D., Guilbe, M.M., Malave, E.C., Hernandez, H.H., Tian, L., Hires, S.A., Marvin, J.S., Looger, L.L., Schreiter, E.R. Crystal structures of the GCaMP calcium sensor reveal the mechanism of fluorescence signal change and aid rational design. J Biol Chem 284, 6455-6464 (2009).
Wiedenmann, J., Ivanchenko, S., Oswald, F., Schmitt, F., Rocker, C., Salih, A., Spindler, K.D., Nienhaus, G.U. EosFP, a fluorescent marker protein with UV-inducible green-to-red fluorescence conversion. Proc Natl Acad Sci U S A 101, 15905-15910 (2004).
Hoi, H., Matsuda, T. Nagai, T., Campbell, R.E. Highlightable Ca2+ indicators for live cell imaging. Journal of the American Chemical Society 135, 46-49 (2013).
Looger, L.L., Griesbeck, O. Genetically encoded neural activity indicators. Current Opinion in Neurobiology 22:18-23 (2012).

* cited by examiner

Averaged traces +/- SEM, N=47 cells, two fields of view

SEQUENCE LISTING

```
<160> NUMBER OF SEQ ID NOS: 13

<210> SEQ ID NO 1
<211> LENGTH: 435
<212> TYPE: PRT
<213> ORGANISM: Artificial Sequence
<220> FEATURE:
<223> OTHER INFORMATION: CaMPARI v1 full-length

<400> SEQUENCE: 1

Met Leu Gln Asn Glu Leu Ala Leu Lys Leu Ala Gly Leu Asp Ile Asn
1               5                   10                  15

Lys Thr Gly Gly Ser His His His His His His Gly Ser Asp Gln Leu
            20                  25                  30

Thr Glu Glu Gln Ile Ala Glu Phe Lys Glu Ala Phe Ser Leu Phe Asp
        35                  40                  45

Lys Asp Gly Asp Gly Thr Ile Thr Thr Lys Glu Leu Gly Thr Val Met
    50                  55                  60

Arg Ser Leu Gly Gln Asn Pro Thr Glu Ala Glu Leu Gln Asp Met Ile
65                  70                  75                  80

Asn Glu Val Asp Ala Asp Gly Asp Gly Thr Ile Asp Phe Pro Glu Phe
                85                  90                  95

Leu Thr Met Met Ala Arg Lys Met Lys Asp Thr Asp Ser Glu Glu Glu
            100                 105                 110
```

```
Ile Arg Glu Ala Phe Arg Val Phe Asp Lys Asp Gly Asn Gly Tyr Ile
            115                 120                 125
Ser Ala Ala Glu Leu Arg His Val Met Thr Asn Leu Gly Glu Lys Leu
        130                 135                 140
Thr Asp Glu Glu Val Asp Glu Met Ile Arg Glu Ala Asp Ile Asp Gly
145                 150                 155                 160
Asp Gly Gln Val Asn Tyr Glu Glu Phe Val Gln Met Met Thr Ala Lys
                165                 170                 175
Leu Glu Cys Glu Lys Ile Tyr Val Arg Asp Gly Val Leu Thr Gly Asp
            180                 185                 190
Ile His Met Ile Leu Leu Leu Glu Gly Asn Ala His Tyr Arg Cys Asp
        195                 200                 205
Phe Arg Thr Thr Tyr Lys Ala Lys Glu Lys Gly Val Lys Leu Pro Gly
210                 215                 220
Val His Phe Val Asp His Cys Ile Glu Ile Leu Ser His Asp Lys Asp
225                 230                 235                 240
Tyr Asn Lys Val Lys Leu Tyr Glu Tyr Ala Val Ala His Ser Gly Leu
                245                 250                 255
Pro Asp Asn Ala Arg Arg Gly Gly Thr Gly Gly Ser Met Val Ser Ala
            260                 265                 270
Ile Lys Pro Asp Met Lys Ile Lys Leu Arg Met Glu Gly Asn Val Asn
        275                 280                 285
Gly His His Phe Val Ile Asp Gly Asp Gly Thr Gly Lys Pro Tyr Glu
290                 295                 300
Gly Lys Gln Thr Met Asp Leu Glu Val Lys Glu Gly Gly Pro Leu Pro
305                 310                 315                 320
Phe Ala Phe Asp Ile Leu Thr Thr Ala Phe His Tyr Gly Asn Arg Val
                325                 330                 335
Phe Val Lys Tyr Pro Asp Asn Ile Gln Asp Tyr Phe Lys Gln Ser Phe
            340                 345                 350
Pro Lys Gly Tyr Ser Trp Glu Arg Ser Met Thr Phe Glu Asp Gly Gly
        355                 360                 365
Ile Cys Tyr Ala Arg Asn Asp Ile Thr Met Glu Gly Asp Thr Phe Tyr
370                 375                 380
Asn Lys Val Arg Phe Tyr Gly Thr Asn Phe Pro Ala Asn Gly Pro Val
385                 390                 395                 400
Met Gln Lys Lys Thr Leu Lys Trp Met Pro Ser Trp Thr Arg Ser Ser
                405                 410                 415
Arg Arg Lys Trp Asn Lys Thr Gly His Ala Val Arg Ala Ile Gly Arg
            420                 425                 430
Leu Ser Ser
        435

<210> SEQ ID NO 2
<211> LENGTH: 84
<212> TYPE: PRT
<213> ORGANISM: Artificial Sequence
<220> FEATURE:
<223> OTHER INFORMATION: Eos C-Terminus Portion of CaMPARI v1

<400> SEQUENCE: 2

Cys Glu Lys Ile Tyr Val Arg Asp Gly Val Leu Thr Gly Asp Ile His
1               5                   10                  15
Met Ile Leu Leu Leu Glu Gly Asn Ala His Tyr Arg Cys Asp Phe Arg
            20                  25                  30
```

Thr Thr Tyr Lys Ala Lys Glu Lys Gly Val Lys Leu Pro Gly Val His
            35                  40                  45

Phe Val Asp His Cys Ile Glu Ile Leu Ser His Asp Lys Asp Tyr Asn
 50                  55                  60

Lys Val Lys Leu Tyr Glu Tyr Ala Val Ala His Ser Gly Leu Pro Asp
 65                  70                  75                  80

Asn Ala Arg Arg

<210> SEQ ID NO 3
<211> LENGTH: 144
<212> TYPE: PRT
<213> ORGANISM: Artificial Sequence
<220> FEATURE:
<223> OTHER INFORMATION: Eos N-Terminus Portion of CaMPARI v1

<400> SEQUENCE: 3

Met Val Ser Ala Ile Lys Pro Asp Met Lys Ile Lys Leu Arg Met Glu
 1               5                  10                  15

Gly Asn Val Asn Gly His His Phe Val Ile Asp Gly Asp Gly Thr Gly
                20                  25                  30

Lys Pro Tyr Glu Gly Lys Gln Thr Met Asp Leu Glu Val Lys Glu Gly
            35                  40                  45

Gly Pro Leu Pro Phe Ala Phe Asp Ile Leu Thr Thr Ala Phe His Tyr
 50                  55                  60

Gly Asn Arg Val Phe Val Lys Tyr Pro Asp Asn Ile Gln Asp Tyr Phe
 65                  70                  75                  80

Lys Gln Ser Phe Pro Lys Gly Tyr Ser Trp Glu Arg Ser Met Thr Phe
                85                  90                  95

Glu Asp Gly Gly Ile Cys Tyr Ala Arg Asn Asp Ile Thr Met Glu Gly
            100                 105                 110

Asp Thr Phe Tyr Asn Lys Val Arg Phe Tyr Gly Thr Asn Phe Pro Ala
            115                 120                 125

Asn Gly Pro Val Met Gln Lys Lys Thr Leu Lys Trp Met Pro Ser Trp
            130                 135                 140

<210> SEQ ID NO 4
<211> LENGTH: 147
<212> TYPE: PRT
<213> ORGANISM: Artificial Sequence
<220> FEATURE:
<223> OTHER INFORMATION: CaM Polypeptide of CaMPARI v1

<400> SEQUENCE: 4

Asp Gln Leu Thr Glu Glu Gln Ile Ala Glu Phe Lys Glu Ala Phe Ser
 1               5                  10                  15

Leu Phe Asp Lys Asp Gly Asp Gly Thr Ile Thr Thr Lys Glu Leu Gly
                20                  25                  30

Thr Val Met Arg Ser Leu Gly Gln Asn Pro Thr Glu Ala Glu Leu Gln
            35                  40                  45

Asp Met Ile Asn Glu Val Asp Ala Asp Gly Asp Gly Thr Ile Asp Phe
 50                  55                  60

Pro Glu Phe Leu Thr Met Met Ala Arg Lys Met Lys Asp Thr Asp Ser
 65                  70                  75                  80

Glu Glu Glu Ile Arg Glu Ala Phe Arg Val Phe Asp Lys Asp Gly Asn
                85                  90                  95

Gly Tyr Ile Ser Ala Ala Glu Leu Arg His Val Met Thr Asn Leu Gly
            100                 105                 110

```
Glu Lys Leu Thr Asp Glu Glu Val Asp Glu Met Ile Arg Glu Ala Asp
            115                 120                 125

Ile Asp Gly Asp Gly Gln Val Asn Tyr Glu Glu Phe Val Gln Met Met
    130                 135                 140

Thr Ala Lys
145

<210> SEQ ID NO 5
<211> LENGTH: 21
<212> TYPE: PRT
<213> ORGANISM: Artificial Sequence
<220> FEATURE:
<223> OTHER INFORMATION: M13 Polypeptide of CaMPARI v1

<400> SEQUENCE: 5

Ser Ser Arg Arg Lys Trp Asn Lys Thr Gly His Ala Val Arg Ala Ile
1               5                   10                  15

Gly Arg Leu Ser Ser
            20

<210> SEQ ID NO 6
<211> LENGTH: 19
<212> TYPE: PRT
<213> ORGANISM: Artificial Sequence
<220> FEATURE:
<223> OTHER INFORMATION: Nuclear Export Signal of CaMPARI v1

<400> SEQUENCE: 6

Met Leu Gln Asn Glu Leu Ala Leu Lys Leu Ala Gly Leu Asp Ile Asn
1               5                   10                  15

Lys Thr Gly

<210> SEQ ID NO 7
<211> LENGTH: 1308
<212> TYPE: DNA
<213> ORGANISM: Artificial Sequence
<220> FEATURE:
<223> OTHER INFORMATION: CaMPARI v1 cDNA Sequence

<400> SEQUENCE: 7
atgctgcaga acgagcttgc tcttaagttg ctggacttg  atattaacaa gactggaggt    60
tctcatcatc accaccacca tggatccgac caactgactg aagagcagat cgcagaattt   120
aaagaggctt tctccctatt tgacaaggac ggggatggga caataacaac caaggagctg   180
gggacggtga tgcggtctct ggggcagaac cccacagaag cagagctgca ggacatgatc   240
aatgaagtag atgccgacgg tgacggcaca atcgacttcc ctgagttcct gacaatgatg   300
gcaagaaaaa tgaaagacac agacagtgaa gaagaaatta gagaagcgtt ccgtgtgttt   360
gataaggatg gcaatggcta catcagtgca gcagagcttc gccacgtgat gacaaacctt   420
ggagagaagt taacagatga agaggttgat gaaatgatca gggaagcaga catcgatggg   480
gatggtcagg taaactacga gagtttgta  caaatgatga cagcgaagct cgagtgcgag   540
aaaatctatg tgcgtgatgg agtgctgacg ggtgatattc atatgatctt gttgcttgaa   600
ggaaatgccc attaccgatg tgacttcaga actacttaca agctaagga  gaagggtgtc   660 aagttaccag gcgtgcactt tgtggaccac tgcattgaga ttttaagcca tgacaaagat   720
tacaacaagg ttaagctgta tgagtatgct gttgctcatt ctggattgcc tgacaatgcc   780
agacgaggcg gtaccggcgg atccatggtg agtgcgatta gccagacat  gaagatcaaa   840 ctccgtatgg aaggcaacgt aaacgggcac cactttgtga tcgacggaga tggtacaggc   900
```

```
aagccttatg agggaaaaca gaccatggat cttgaagtca agagggcgg acctctgcct    960 tttgcctttg atatcctgac cactgcattc cattacggca acagggtatt cgtgaaatat   1020
ccagacaaca tacaagacta ttttaagcag tcgtttccta agggtattc gtgggaacga    1080 agcatgactt tcgaagacgg gggcatttgc tatgccagaa cgacataac aatggaaggg    1140 gacactttct ataataaagt tcgattttat ggtaccaact ttcccgccaa tggtccagtt   1200
atgcagaaga gacgctgaa atggatgccg agctggacgc gttcatcacg tcgtaagtgg    1260
aataagacag gtcacgcagt cagagctata ggtcggctga gctcataa               1308
```

<210> SEQ ID NO 8
<211> LENGTH: 415
<212> TYPE: PRT
<213> ORGANISM: Artificial Sequence
<220> FEATURE:
<223> OTHER INFORMATION: CaMPARI Fragment

<400> SEQUENCE: 8

```
Met His His His His His Gly Ser Ser Arg Arg Lys Trp Asn
1               5                  10                  15

Lys Thr Gly His Ala Val Arg Ala Ile Gly Arg Leu Ser Ser Leu Glu
            20                  25                  30

Gly Glu Lys Met Tyr Val Arg Asp Gly Val Leu Thr Gly Asp Ile His
        35                  40                  45

Met Ala Leu Leu Leu Glu Gly Asn Ala His Tyr Arg Cys Asp Phe Arg
    50                  55                  60

Thr Thr Tyr Lys Ala Lys Glu Lys Gly Val Lys Leu Pro Gly Tyr His
65                  70                  75                  80

Phe Val Asp His Cys Ile Glu Ile Leu Ser His Asp Lys Asp Tyr Asn
                85                  90                  95

Lys Val Lys Leu Tyr Glu His Ala Val Ala His Ser Gly Leu Pro Asp
            100                 105                 110

Asn Ala Arg Arg Gly Gly Thr Gly Gly Ser Met Val Ser Ala Ile Lys
        115                 120                 125

Pro Asp Met Lys Ile Lys Leu Arg Met Glu Gly Asn Val Asn Gly His
    130                 135                 140

His Phe Val Ile Asp Gly Asp Gly Thr Gly Lys Pro Tyr Glu Gly Lys
145                 150                 155                 160

Gln Thr Met Asp Leu Glu Val Lys Glu Gly Gly Pro Leu Pro Phe Ala
                165                 170                 175

Phe Asp Ile Leu Thr Thr Ala Phe His Tyr Gly Asn Arg Val Phe Val
            180                 185                 190

Lys Tyr Pro Asp Asn Ile Gln Asp Tyr Phe Lys Gln Ser Phe Pro Lys
        195                 200                 205

Gly Tyr Ser Trp Glu Arg Ser Leu Thr Phe Glu Asp Gly Gly Ile Cys
    210                 215                 220

Tyr Ala Arg Asn Asp Ile Thr Met Glu Gly Asp Thr Phe Tyr Asn Lys
225                 230                 235                 240

Val Arg Phe Tyr Gly Thr Asn Phe Pro Ala Asn Gly Pro Val Met Gln
                245                 250                 255

Lys Lys Thr Leu Lys Trp Glu Pro Ser Thr Thr Arg Asp Gln Leu Thr
            260                 265                 270

Glu Glu Gln Ile Ala Glu Phe Lys Glu Ala Phe Ser Leu Phe Asp Lys
        275                 280                 285

Asp Gly Asp Gly Thr Ile Thr Thr Lys Glu Leu Gly Thr Val Met Arg
```

Ser Leu Gly Gln Asn Pro Thr Glu Ala Glu Leu Gln Asp Met Ile Asn
305                 310                 315                 320

Glu Val Asp Ala Asp Gly Asp Gly Thr Ile Asp Phe Pro Glu Phe Leu
            325                 330                 335

Thr Met Met Ala Arg Lys Met Lys Asp Thr Asp Ser Glu Glu Glu Ile
        340                 345                 350

Arg Glu Ala Phe Arg Val Phe Asp Lys Asp Gly Asn Gly Tyr Ile Ser
    355                 360                 365

Ala Ala Glu Leu Arg His Val Met Thr Asn Leu Gly Glu Lys Leu Thr
370                 375                 380

Asp Glu Glu Val Asp Glu Met Ile Arg Glu Ala Asp Ile Asp Gly Asp
385                 390                 395                 400

Gly Gln Val Asn Tyr Glu Glu Phe Val Gln Met Met Thr Ala Lys
                405                 410                 415

<210> SEQ ID NO 9
<211> LENGTH: 1248
<212> TYPE: DNA
<213> ORGANISM: Artificial Sequence
<220> FEATURE:
<223> OTHER INFORMATION: CaMPARI Fragment DNA

<400> SEQUENCE: 9

```
atgcatcatc accaccacca tggatcctca tcacgtcgta agtggaataa gacaggtcac      60
gcagtcagag ctataggtcg gctgagctca ctcgagggcg agaaaatgta tgtgcgtgat     120
ggagtgctga cgggtgatat tcatatggct ttgttgcttg aaggaaatgc ccattaccga     180
tgtgacttca gaactactta caaagctaag gagaagggtg tcaagttacc aggctaccac     240
tttgtggacc actgcattga dattttaagc catgacaaag attacaacaa ggttaagctg     300
tatgagcatg ctgttgctca ttctggattg cctgacaatg ccagacgagg cggtaccgga     360
gggagcatgg tgagtgcgat taagccagac atgaagatca aactccgtat ggaaggcaac     420
gtaaacgggc accactttgt gatcgacgga gatggtacag gcaagcctta tgagggaaaa     480
cagaccatgg atcttgaagt caaagagggc ggacctctgc cttttgcctt tgatatcctg     540
accactgcat tccattacgg caacagggta ttcgtgaaat atccagacaa catacaagac     600
tattttaagc agtcgtttcc taaggggtat tcgtgggaac gaagcttgac tttcgaagac     660
gggggcattt gctatgccag aaacgacata acaatggaag gggacacttt ctataataaa     720
gttcgatttt atggtaccaa ctttcccgcc aatggtccag ttatgcagaa gagacgctg      780
aaatgggagc cctccaccac gcgtgaccaa ctgactgaag agcagatcgc agaatttaaa     840
gaggctttct ccctatttga caaggacggg gatgggacaa taacaaccaa ggagctgggg     900
acggtgatgc ggtctctggg gcagaacccc acagaagcag agctgcagga catgatcaat     960
gaagtagatg ccgacggtga cggcacaatc gacttccctg agttcctgac aatgatggca    1020
agaaaaatga agacacaga cagtgaagaa gaaattagag aagcgttccg tgtgtttgat    1080
aaggatggca atggctacat cagtgcagca gagcttcgcc acgtgatgac aaaccttgga    1140
gagaagttaa cagatgaaga ggttgatgaa atgatcaggg aagcagacat cgatggggat    1200
ggtcaggtaa actacgaaga gtttgtacaa atgatgacag cgaagtaa                 1248
```

<210> SEQ ID NO 10
<211> LENGTH: 414
<212> TYPE: PRT

<213> ORGANISM: Artificial Sequence
<220> FEATURE:
<223> OTHER INFORMATION: EosFP Circularly Permutated Beta Strand 8

<400> SEQUENCE: 10

```
Met His His His His His Gly Ser Ser Arg Arg Lys Trp Asn
1               5                   10                  15

Lys Thr Gly His Ala Val Arg Ala Ile Gly Arg Leu Ser Ser Leu Glu
                20                  25                  30

Arg Met Ala Leu Leu Leu Glu Gly Asn Ala His Tyr Arg Cys Asp Phe
            35                  40                  45

Arg Thr Thr Tyr Lys Ala Lys Glu Lys Gly Val Lys Leu Pro Gly Tyr
50                  55                  60

His Phe Val Asp His Cys Ile Glu Ile Leu Ser His Asp Lys Asp Tyr
65                  70                  75                  80

Asn Lys Val Lys Leu Tyr Glu His Ala Val Ala His Ser Gly Leu Pro
                85                  90                  95

Asp Asn Ala Arg Arg Gly Gly Thr Gly Gly Ser Met Val Ser Ala Ile
            100                 105                 110

Lys Pro Asp Met Lys Ile Lys Leu Arg Met Glu Gly Asn Val Asn Gly
        115                 120                 125

His His Phe Val Ile Asp Gly Asp Gly Thr Gly Lys Pro Tyr Glu Gly
    130                 135                 140

Lys Gln Thr Met Asp Leu Glu Val Lys Glu Gly Gly Pro Leu Pro Phe
145                 150                 155                 160

Ala Phe Asp Ile Leu Thr Thr Ala Phe His Tyr Gly Asn Arg Val Phe
                165                 170                 175

Val Lys Tyr Pro Asp Asn Ile Gln Asp Tyr Phe Lys Gln Ser Phe Pro
            180                 185                 190

Lys Gly Tyr Ser Trp Glu Arg Ser Met Thr Phe Glu Asp Gly Gly Ile
        195                 200                 205

Cys Tyr Ala Arg Asn Asp Ile Thr Met Glu Gly Asp Thr Phe Tyr Asn
    210                 215                 220

Lys Val Arg Phe Tyr Gly Thr Asn Phe Pro Ala Asn Gly Pro Val Met
225                 230                 235                 240

Gln Lys Lys Thr Leu Lys Trp Glu Pro Ser Thr Glu Lys Met Tyr Val
                245                 250                 255

Arg Asp Gly Val Leu Thr Gly Asp Ser Thr Arg Asp Gln Leu Thr Glu
            260                 265                 270

Glu Gln Ile Ala Glu Phe Lys Glu Ala Phe Ser Leu Phe Asp Lys Asp
        275                 280                 285

Gly Asp Gly Thr Ile Thr Thr Lys Glu Leu Gly Thr Val Met Arg Ser
    290                 295                 300

Leu Gly Gln Asn Pro Thr Glu Ala Glu Leu Gln Asp Met Ile Asn Glu
305                 310                 315                 320

Val Asp Ala Asp Gly Asp Gly Thr Ile Asp Phe Pro Glu Phe Leu Thr
                325                 330                 335

Met Met Ala Arg Lys Met Lys Asp Thr Asp Ser Glu Glu Ile Arg
            340                 345                 350

Glu Ala Phe Arg Val Phe Asp Lys Asp Gly Asn Gly Tyr Ile Ser Ala
        355                 360                 365

Ala Glu Leu Arg His Val Met Thr Asn Leu Gly Glu Lys Leu Thr Asp
    370                 375                 380

Glu Glu Val Asp Glu Met Ile Arg Glu Ala Asp Ile Asp Gly Asp Gly
```

```
                385                 390                 395                 400

Gln Val Asn Tyr Glu Glu Phe Val Gln Met Met Thr Ala Lys
                    405                 410

<210> SEQ ID NO 11
<211> LENGTH: 1245
<212> TYPE: DNA
<213> ORGANISM: Artificial Sequence
<220> FEATURE:
<223> OTHER INFORMATION: EosFP Circularly Permutated Beta Strand 8

<400> SEQUENCE: 11
atgcatcatc accaccacca tgatcctca  tcacgtcgta agtggaataa gacaggtcac      60
gcagtcagag ctataggtcg gctgagctca ctcgagcgga tggcgttgtt gcttgaagga     120
aatgcccatt accgatgtga cttcagaact acttacaaag ctaaggagaa gggtgtcaag     180
ttaccaggct accactttgt ggaccactgc attgagattt aagccatga  caaagattac     240 aacaaggtta agctgtatga gcatgctgtt gctcattctg gattgcctga caatgccaga     300
cgaggcggta ccggcggatc catggtgagt gcgattaagc agacatgaa  gatcaaactc     360 cgtatggaag gcaacgtaaa cgggcaccac tttgtgatcg acggagatgg tacaggcaag     420
ccttatgagg gaaaacagac catggatctt gaagtcaaag agggcggacc tctgccttt     480 gcctttgata tcctgaccac tgcattccat tacggcaaca gggtattcgt gaaatatcca     540
gacaacatac aagactattt taagcagtcg tttcctaagg ggtattcgtg ggaacgaagc     600
atgactttcg aagacggggg catttgctat gccagaaacg acataacaat ggaaggggac     660
actttctata ataaagttcg attttatggt accaactttc ccgccaatgg tccagttatg     720
cagaagaaga cgctgaaatg ggagccctcc actgagaaaa tgtatgtgcg tgatggagtg     780
ctgacgggtg actccacgcg tgaccaactg actgaagagc agatcgcaga atttaaagag     840
gctttctccc tatttgacaa ggacgggaat gggacaataa aaccaagga  gctggggacg     900 gtgatgcggt ctctggggca gaaccccaca gaagcagagc tgcaggacat gatcaatgaa     960
gtagatgccg acggtgacgg cacaatcgac ttccctgagt tcctgacaat gatggcaaga    1020
aaaatgaaag acacagacag tgaagaagaa attagagaag cgttccgtgt gtttgataag    1080
gatggcaatg gctacatcag tgcagcagag cttcgccacg tgatgacaaa ccttggagag    1140
aagttaacag atgaagaggt tgatgaaatg atcagggaag cagacatcga tgggatggt    1200 caggtaaact acgaagagtt tgtacaaatg atgacagcga agtaa                   1245

<210> SEQ ID NO 12
<211> LENGTH: 415
<212> TYPE: PRT
<213> ORGANISM: Artificial Sequence
<220> FEATURE:
<223> OTHER INFORMATION: CaMPARI v0.1

<400> SEQUENCE: 12

Met His His His His His His Gly Ser Asp Gln Leu Thr Glu Glu Gln
1               5                   10                  15

Ile Ala Glu Phe Lys Glu Ala Phe Ser Leu Phe Asp Lys Asp Gly Asp
                20                  25                  30

Gly Thr Ile Thr Thr Lys Glu Leu Gly Thr Val Met Arg Ser Leu Gly
            35                  40                  45

Gln Asn Pro Thr Glu Ala Glu Leu Gln Asp Met Ile Asn Glu Val Asp
        50                  55                  60
```

Ala Asp Gly Asp Gly Thr Ile Asp Phe Pro Glu Phe Leu Thr Met Met
 65                  70                  75                  80

Ala Arg Lys Met Lys Asp Thr Asp Ser Glu Glu Glu Ile Arg Glu Ala
                 85                  90                  95

Phe Arg Val Phe Asp Lys Asp Gly Asn Gly Tyr Ile Ser Ala Ala Glu
            100                 105                 110

Leu Arg His Val Met Thr Asn Leu Gly Glu Lys Leu Thr Asp Glu Glu
        115                 120                 125

Val Asp Glu Met Ile Arg Glu Ala Asp Ile Asp Gly Asp Gly Gln Val
    130                 135                 140

Asn Tyr Glu Glu Phe Val Gln Met Met Thr Ala Lys Leu Glu Cys Glu
145                 150                 155                 160

Lys Met Tyr Val Arg Asp Gly Val Leu Thr Gly Asp Ile His Met Ala
                165                 170                 175

Leu Leu Leu Glu Gly Asn Ala His Tyr Arg Cys Asp Phe Arg Thr Thr
            180                 185                 190

Tyr Lys Ala Lys Glu Lys Gly Val Lys Leu Pro Gly Tyr His Phe Val
        195                 200                 205

Asp His Cys Ile Glu Ile Leu Ser His Asp Lys Asp Tyr Asn Lys Val
    210                 215                 220

Lys Leu Tyr Glu His Ala Val Ala His Ser Gly Leu Pro Asp Asn Ala
225                 230                 235                 240

Arg Arg Gly Gly Thr Gly Gly Ser Met Val Ser Ala Ile Lys Pro Asp
                245                 250                 255

Met Lys Ile Lys Leu Arg Met Glu Gly Asn Val Asn Gly His His Phe
            260                 265                 270

Val Ile Asp Gly Asp Gly Thr Gly Lys Pro Tyr Glu Gly Lys Gln Thr
        275                 280                 285

Met Asp Leu Glu Val Lys Glu Gly Gly Pro Leu Pro Phe Ala Phe Asp
    290                 295                 300

Ile Leu Thr Thr Ala Phe His Tyr Gly Asn Arg Val Phe Val Lys Tyr
305                 310                 315                 320

Pro Asp Asn Ile Gln Asp Tyr Phe Lys Gln Ser Phe Pro Lys Gly Tyr
                325                 330                 335

Ser Trp Glu Arg Ser Met Thr Phe Glu Asp Gly Gly Ile Cys Tyr Ala
            340                 345                 350

Arg Asn Asp Ile Thr Met Glu Gly Asp Thr Phe Tyr Asn Lys Val Arg
        355                 360                 365

Phe Tyr Gly Thr Asn Phe Pro Ala Asn Gly Pro Val Met Gln Lys Lys
    370                 375                 380

Thr Leu Lys Trp Glu Pro Ser Trp Thr Arg Ser Ser Arg Arg Lys Trp
385                 390                 395                 400

Asn Lys Thr Gly His Ala Val Arg Ala Ile Gly Arg Leu Ser Ser
                405                 410                 415

<210> SEQ ID NO 13
<211> LENGTH: 6
<212> TYPE: PRT
<213> ORGANISM: Artificial Sequence
<220> FEATURE:
<223> OTHER INFORMATION: Synthesized linker

<400> SEQUENCE: 13

Gly Gly Thr Gly Gly Ser
1               5

FLUORESCENT PROTEIN-BASED CALCIUM INTEGRATORS

RELATED APPLICATIONS

This application claims priority from U.S. Provisional Patent Application No. 61/862,436, filed Aug. 5, 2014, the entire disclosure of which is incorporated herein by this reference.

TECHNICAL FIELD

The presently-disclosed subject matter relates to fluorescent compositions. In particular, the presently-disclosed subject matter relates to fluorescent protein-based calcium indicators.

INTRODUCTION

Brain function is dictated by patterns of synaptic input and action potential firing, each of which is accompanied by transient increases in free cytoplasmic $Ca^{2+}$. The tools used currently to research the calcium ion include synthetic organic dyes and engineered fluorescent proteins. That said, synthetic dyes can be phototoxic, invasive, and bleached over time limiting their usefulness. Genetically encoded calcium indicators (GECIs) are also broadly useful for monitoring the activity of populations of neurons and synapses in behaving model organisms. However, the transient nature of GECI responses following $[Ca^{2+}]$ rises requires continuous monitoring during behavior using sophisticated imaging equipment with limited fields of view, and often with physical restraint (i.e. head fixation, paralysis) and by 2-photon microscopy through a cranial window.

Alternatively, post hoc staining of immediate early genes (IEGs) expression (protein or mRNA) such as Arc and c-Fos can be measured following free behavior with a lifetime of several hours, but has poor temporal resolution, is only weakly correlated with neural electrical activity, and is constrained neither by genetic cell type nor by experimental window. Attempts to genetically target and gate IEG reporters have thus far been minimally successful.

Hence, there remains the need for compositions that can genetically target direct reporters of neural activity (e.g., voltage or $[Ca^{2+}]$) and that can be rendered permanent for post hoc analysis, thereby reducing or eliminating the time pressures associated with analyzing probed samples. There also remains a need for compositions that can mark neurons active during short user-defined behavioral epochs.

BRIEF DESCRIPTION OF THE DRAWINGS

The novel features of the presently-disclosed subject matter are set forth with particularity in the appended claims. A better understanding of the features and advantages of the presently-disclosed subject matter will be obtained by reference to the following detailed description that sets forth illustrative embodiments, in which the principles of the presently-disclosed subject matter are used, and the accompanying drawings of which:

BRIEF DESCRIPTION OF THE SEQUENCE LISTING

Figure 1A:
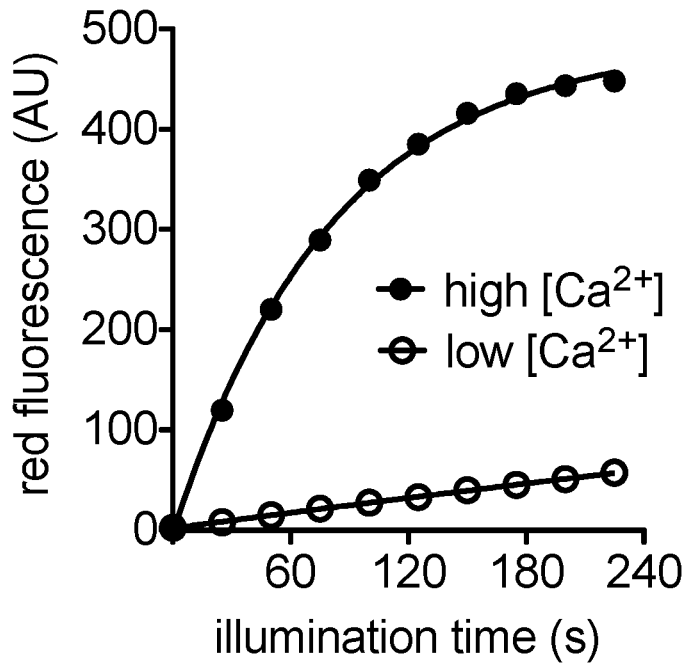
FIGS. 1A and 1B include plots showing (A) the amount of red fluorescence present after exposure to photoconversion light in the presence or absence of calcium as a function of time (lines are single exponential fits to the data, from which the rates were calculated), and (B) the CaMPARI photoconversion rate as a function of different concentrations of free calcium ions (black line represents a sigmoidal fit to the data).

SEQ ID NO: 1 is an amino acid sequence encoding an embodiment of an isolated polypeptide comprising CaM, EosFP, and M13, or fragments and/or variants thereof (i.e., CaMPARI v1);

SEQ ID NO: 2 is an amino acid sequence encoding an mEos C-terminus portion of CaMPARI v1;

SEQ ID NO: 3 is an amino acid sequence encoding an mEos N-terminus portion of CaMPARI v1;

SEQ ID NO: 4 is an amino acid sequence encoding CaM portion of CaMPARI v1;

SEQ ID NO: 5 is an amino acid sequence encoding M13 portion of CaMPARI v1;

SEQ ID NO: 6 is an amino acid sequence encoding nuclear export sequence (NES) portion of CaMPARI v1;

SEQ ID NO: 7 is a cDNA sequence encoding the isolated polypeptide of SEQ ID NO: 1;

SEQ ID NO: 8 is an amino acid sequence encoding another embodiment of an isolated polypeptide comprising CaM, EosFP, and M13, or fragments and/or variants thereof;

SEQ ID NO: 9 is a cDNA sequence encoding the isolated polypeptide of SEQ ID NO: 8;

SEQ ID NO: 10 is an amino acid sequence encoding another embodiment of an isolated polypeptide comprising CaM, EosFP, and M13, the EosFP including a circular permutation within beta strand number 8; and SEQ ID NO: 11 is a cDNA sequence encoding the isolated polypeptide of SEQ ID NO: 10.

SEQ ID NO: 12 is an amino acid sequence encoding yet another embodiment of an isolated polypeptide.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter includes isolated polypeptides that can be used to detect ions, small molecule analytes, and/or cellular states such as membrane potential (e.g., voltage). The presently-disclosed subject matter also includes polynucleotides (e.g., cDNA) encoding the presently-disclosed isolated polypeptides. Furthermore, the presently-disclosed subject matter includes methods of using the presently-disclosed isolated polypeptides to detect ions, small molecule analytes, and/or cellular states such as membrane potential. Further still, the presently-disclosed subject matter includes methods for making the presently-disclosed isolated polypeptides.

The term "isolated", when used in the context of an isolated nucleotide or an isolated polypeptide, is a nucleotide or polypeptide that, by the hand of man, exists apart from its native environment and is therefore not a product of nature. An isolated nucleotide or polypeptide can exist in a purified form or can exist in a non-native environment such as, for example, in a transgenic host cell. The term "native" or "wild type" refers to a gene that is naturally present in the genome of an untransformed cell. Similarly, when used in the context of a polypeptide, "native" or "wild type" refers to a polypeptide that is encoded by a native gene of an untransformed cell's genome.

Additionally, the terms "polypeptide", "protein", and "peptide", which are used interchangeably herein, refer to a polymer of the protein amino acids, or amino acid analogs, regardless of its size or function. Although "protein" is often used in reference to relatively large polypeptides, and "peptide" is often used in reference to small polypeptides, usage of these terms in the art overlaps and varies. The term "polypeptide" as used herein refers to peptides, polypeptides, and proteins, unless otherwise noted. The terms "protein", "polypeptide", and "peptide" are used interchangeably herein when referring to a gene product. Thus, exemplary polypeptides include gene products, naturally occurring proteins, homologs, orthologs, paralogs, fragments and other equivalents, variants, and analogs of the foregoing. The term "fusion polypeptide" and the like refer to a polypeptide that is comprised of two or more distinct polypeptides that are covalently bound.

In some embodiments the isolated polypeptides comprise a fluorescent polypeptide, a compound-binding polypeptide, and a polypeptide target of the compound-binding (or voltage-sensing) polypeptide (polypeptide target), as well as variants and/or fragments of any of the polypeptides. The individual polypeptides that comprise the isolated polypeptide can be arranged in any fashion. For instance, some embodiments of isolated polypeptide can comprise, from the N-terminus to C-terminus, the compound-binding polypeptide, the fluorescent polypeptide, and the polypeptide target. In other embodiments the isolated polypeptide can comprise, from the C-terminus to N-terminus, the compound-binding polypeptide, the fluorescent polypeptide, and the polypeptide target. In this regard, even if not specifically set forth herein, embodiments of the presently-disclosed polypeptides include fusion polypeptides.

The term "variant" refers to an amino acid sequence that is different from the reference polypeptide sequence by the location or type of one or more amino acids. Thus, a variant may include one or more amino acid substitutions. The terms "polypeptide fragment" or "fragment", when used in reference to a reference polypeptide, refer to a polypeptide in which amino acid residues are deleted as compared to the reference (e.g., native) polypeptide itself, but where the remaining amino acid sequence is usually identical to the corresponding positions in the reference polypeptide. As mentioned above, in some instances such deletions can occur at the amino-terminus, carboxy-terminus of the reference polypeptide, or alternatively both.

A fragment can also be a "functional fragment," in which case the fragment retains some or all of the activity of the reference polypeptide as described herein. For instance, a functional fragment of a fluorescent polypeptide can retain some or all of its fluorescent properties, and in some instances the fluorescent properties can be enhanced relative to the reference (e.g., native) fluorescent polypeptide.

With respect to the fluorescent polypeptides (FP), the fluorescent polypeptides described herein generally include polypeptides comprising a chromophore. After synthesis and folding of the isolated polypeptide, the chromophore can emit a fluorescence. The chromophore can be an amino acid segment, including the amino acid segment HYG. Fluorescent polypeptides can experience a particular photoconvertible color shift when the isolated polypeptides contact a detecting substance, such as a particular ion or small molecule analyte. In some embodiments the fluorescent polypeptides can experience a particular photoconvertible color shift when a cellular condition, such as membrane depolarization, occurs.

Therefore, in some embodiments of the isolated polypeptides the fluorescent polypeptides can include photoconvertible fluorescent proteins. There is no particular limitation on the color shift that the photoconvertible fluorescent proteins can exhibit. Exemplary photoconvertible fluorescent proteins include, but are not limited to, PS-CFP (cyan-to-green photoconversion) and PSmOrange (orange-to-far red photoconversion) polypeptides. The fluorescent polypeptides also include green-to-red polypeptides including, but not limited to, Kaede, Kikume, KikGR, mClavGR2, mMaple, Dendra, IrisFP, and NijiFP. See also, for example, the fluorescent polypeptides described in U.S. Patent Application Publication No. 2011/0214192 to Wang et al.

Additionally or alternatively, in some embodiments the fluorescent polypeptides are selected from dim-to-bright photoactivatable fluorescent polypeptides. Exemplary dimto-bright photoactivatable fluorescent polypeptides include, but are not limited to, PA-GFP and PAmCherry. Similar to color shifting fluorescent polypeptides, the extent to which dim-to-bright polypeptides undergo photoactivation can depend on the concentration of a detecting substance (e.g., ion or analyte) and/or cellular condition, such as membrane potential.

In some embodiments the fluorescent polypeptide is an Eos fluorescent polypeptide (FP), or a fragment and/or variant thereof. In some embodiments the fluorescent polypeptide can be circularly permutated and/or comprise amino acid substitutions. In some embodiments the EosFP is a circularly permutated mEos2 polypeptide and/or includes one or more mutations selected from V2ins, F34Y, S39T, A69V, L93M, and I102Y. An exemplary polypeptide comprising circularly permutated mEos2 as well as the mutations V2ins, F34Y, S39T, A69V, L93M, and I102Y is referred to herein as a CaMPARI v1 isolated polypeptide (SEQ ID NO: 1). The amino acid sequence of the exemplary fluorescent polypeptide of CaMPARI v1 is shown in SEQ ID NOS: 2 and 3, which correspond to the C-terminus and N-terminus portions of the fluorescent polypeptide, respectively.

The fluorescent proteins can have circular permutations on beta strands of the polypeptides. In embodied polypeptides that include EosFP, the circular permutations can be on beta strands 1, 5, 7, 8, and/or 9 in certain embodiments. For example, SEQ ID NO: 10 shows an amino acid sequence of an exemplary isolated polypeptide having a circular permutation on beta strand 8 of the EosFP. Those of ordinary skill in the art, upon reviewing the entire disclosure of this paper, will appreciate similar circular permutations or mutations that can be performed on other fluorescent proteins to enhance their ability to detect a substance.

With regard to the compound-binding polypeptides, these polypeptides can be selected from polypeptides that can selectively bind particular substances. The compound-binding polypeptides therefore permit the isolated polypeptide to bind to one or more particular substance. Isolated polypeptides with compound-binding polypeptides can therefore act as an integrator, and possibly also as a negative indicator, for the particular substance that the compound-binding polypeptide can bind to. Exemplary detecting substances that can be bound by compound-binding polypeptides include ions and small molecule analytes. Detecting substances can include substances that have significant roles in cellular pathways.

In some embodiments the compound-binding polypeptide includes a calmodulin (CaM) polypeptide, or variants and/or fragments thereof (e.g., SEQ ID NO: 4). CaM binds to calcium, and permits the isolated polypeptide to act as an integrator for calcium. In turn, calcium detection can be used to trace neurons, measure neuronal activity, or the like.

With regard to the polypeptide targets of the compound-binding polypeptide, these polypeptide target can interact selectively with a compound-binding polypeptide that is bound to a detecting substance. For instance, in an exemplary isolated polypeptide that comprises the compound-binding polypeptide CaM, the polypeptide target can be a M13 polypeptide, or a variant and/or fragment thereof (e.g., SEQ ID NO: 5). M13 can selectively interact with the calcium-bound form of CaM. Some embodiments also comprise variants and/or fragments of any polypeptide target.

Accordingly, in specific embodiments the isolated polypeptide comprises an EosFP polypeptide, a CaM polypeptide, and a M13 polypeptide, or variants and/or fragments thereof. Variants of the present polypeptides that include an EosFP polypeptide, a CaM polypeptide, and a M13 polypeptide can include one or more mutations in the fluorescent peptide selected from V2ins, F34Y, S39T, A69V, D78S, L93M, I102Y, and combinations thereof (see, e.g., SEQ ID NO: 1). Additionally or alternatively, such polypeptides can also include mutations selected from Q171V, Q171T, Q171R, M172R, M172L, M173T, A175L, H194W, F227Y, C231R, C231T, C231A, I232V, I232C, L246I, L281V, N374A, N374S, and combinations thereof. Additionally or alternatively, variants of the present polypeptides that comprise the polypeptide target M13 can include one or more amino acid mutations in the M13 polypeptide selected from S2L, W6Y, W6L, W6V, W6M, W6H, W6F, T9A, T9D, G10D, G10A, H11K, V13H, V13S, V13T, V13A, V13D, V13L, and combinations thereof. Those of ordinary skill in the art will recognize that other embodiments of the present polypeptides can comprise other mutations that yield similar effects as the specific mutations described herein.

In some embodiments, the isolated polypeptide can be a polypeptide having 85, 86, 87, 88, 89, 90, 91, 92, 93, 94, 95, 96, 97, 98, or 99% homology to an isolated polypeptide having the amino acid sequence of a polypeptide that includes an EosFP polypeptide, a CaM polypeptide, and an M13 polypeptide. "Percent similarity" and "percent homology" are synonymous as herein and can be determined, for example, by comparing sequence information using the GAP computer program, available from the University of Wisconsin Geneticist Computer Group. The GAP program utilizes the alignment method of Needleman et al. (1970) *J. Mol. Biol.* 48:443, as revised by Smith et al. (1981) *Adv. Appl. Math.* 2:482. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps. The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

Additionally, in some embodiments the EosFP polypeptide can include a C-terminus portion and an N-terminus portion. Exemplary C-terminus and N-terminus portions of a EosFP polypeptide can comprise the amino acid sequence of, respectively, SEQ ID NO: 2 and SEQ ID NO: 3. Furthermore, the N-terminus portion and the C-terminus portion of any fluorescent polypeptide can be joined together via an inter-domain linker that is disposed therebetween. Exemplary linkers can comprise about 4, 5, 6, 7, 8, 9, 10, 11, 12, 13, 14, 15, 16, 17, 18, 19, or 20 amino acids. In some embodiments the inter-domain linker is six amino acids in length. In certain embodiments the inter-domain linker comprises the amino acid sequence GGTGGS SEQ ID NO: 13.

The order in which the polypeptides that comprise the isolated polypeptide are joined is not particularly limited. In some embodiments the polypeptide comprises the CaM polypeptide, the EosFP polypeptide, and the M13 polypeptide from an N-terminus to a C-terminus of the isolated polypeptide. On the other hand, another exemplary isolated polypeptide can comprise, from a C-terminus to an N-terminus, the CaM polypeptide, the EosFP polypeptide, and the M13 polypeptide. For instance, SEQ ID NOS: 1 and 8 show the amino acid sequences of exemplary isolated polypeptides that, among other things, have opposing orientations of the CaM polypeptide, the EosFP polypeptide, and the M13 polypeptide.

As described herein, the present isolated polypeptides can include fragments of polypeptides. In some embodiments a polypeptide fragment has 1, 2, 3, 4, 5, 6, 7, 8, 9, 10, 11, 12, 13, 14, 15, 16, 17, 18, 19, 20, or more amino acids that are removed relative to a reference sequence. For example, SEQ ID NO: 8 includes the amino acid sequence of an exemplary fragment of the polypeptide having the sequence of SEQ ID NO: 1. In different embodiments of fragments, amino acids can be removed from the N-terminus and/or the C-terminus of the isolated polypeptide and/or any of the individual polypeptides that form the isolated polypeptide.

In some embodiments the isolated polypeptides can comprise one or more linker polypeptides that are disposed between any of the individual polypeptides (e.g., fluorescent polypeptide, compounding binding polypeptide, polypeptide target polypeptide, etc.) that are included in the isolated polypeptide. In some embodiments the isolated polypeptides comprise a first polypeptide linker disposed between the compound-binding polypeptide and the fluorescent polypeptide. Additionally or alternatively, some embodiments comprise a second linker polypeptide disposed between the fluorescent polypeptide and the polypeptide target. The linker polypeptides can be provided for the purpose of purifying the isolated polypeptide, among other things. For instance, in some embodiments at least one of the linker polypeptides is a hexahistidine tag (6×His tag) that can be used to purify the protein using affinity chromatography. In some embodiments at least one linker can be a restriction site used in the assembly of DNA, such as XhoI or MluI. Those of ordinary skill will appreciate other linker polypeptides that can be incorporated into the isolated polypeptides for purification purposes, as restriction sites, or the like.

The present isolated polypeptides can also comprise a nuclear export signal (NES). The NES can signal for export of the isolated protein from the cell nucleus. Consequently, the addition of a NES can, among other things, allow the isolated polypeptide to detect substances outside the cell nucleus. The NES may be located at the N-terminus or the C-terminus of the isolated polypeptide. One exemplary NES is one that comprises an amino acid sequence of SEQ ID NO: 6.

The presently-disclosed subject matter also includes nucleic acid molecules (e.g., cDNA) that encode an isolated polypeptide. In some embodiments the nucleic acid molecule comprises a nucleic acid molecule encoding a polypeptide that comprises CaM, EosFP, and M13, or mutations and/or fragments thereof. Exemplary nucleic acid sequences include those represented by SEQ ID NOS: 7, 9, and 10. In certain embodiments the nucleic acid molecule that encodes the isolated peptide is cDNA. Thus, embodiments of the nucleic acid molecules described herein only include the exon portions capable of sequencing one of the presently-described isolated polypeptides.

The terms "nucleotide," "polynucleotide," "nucleic acid," "nucleic acid sequence," and the like refer to deoxyribonucleotides or ribonucleotides and polymers thereof in either single or double stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified versions thereof (e.g., degenerate codon substitutions) and complementary sequences and as well as the sequence explicitly indicated. Specifically, degenerate codon substitutions can be achieved by generating sequences in which the third position of one or more selected (or all) codons is substituted with mixed base and/or deoxyinosine residues (Batzer et al. (1991) Nucleic Acid Res 19:5081; Ohtsuka et al. (1985) J Biol Chem 260:2605 2608; Rossolini et al. (1994) Mol Cell Probes 8:91 98). The terms are inclusive of cDNA molecules.

In some embodiments the nucleic acid molecule is a molecule that encodes portions of an isolated polypeptide, including any of the portions described herein. For instance, the nucleic acid molecule may encode for a compound-binding polypeptide (e.g., CaM), a fluorescent polypeptide (e.g., EosFP), and/or a polypeptide target (e.g., M13). Other embodiments of nucleic acid molecules can encode for the first polypeptide linker, the second polypeptide linker, the inter-domain linker, the NES, or any combination thereof of any of the isolated polypeptides described herein.

Further still, the presently-disclosed subject matter includes a method of detecting an ion and/or small molecule analyte (collectively referred to herein as "detecting substance") in a sample. Exemplary detecting substances include, but are not limited to, calcium, glutamate, gamma-aminobutyric acid, glycine, acetylcholine, dopamine, other neurotransmitters and neuromodulators, ATP, ADP, cAMP, cGMP, sugars such as glucose, inositol phosphates such as IP3, diacylglycerol, other metabolites and signaling molecules, zinc, iron, potassium, magnesium, other ions, proteins, and combinations thereof. Additionally or alternatively, some methods of the presently-disclosed subject matter include methods of detecting a cellular state. Exemplary cellular states that can be detected include, but are not limited to, membrane potential, kinase activity, G-protein coupled receptor (GPCR) activation, ion channel activity, transporter activity, and combinations thereof.

In some embodiments the method comprises providing a sample that includes cells, contacting the sample with an embodiment of the present isolated polypeptides, exposing the sample that has contacted the isolated polypeptide to light, and then detecting the presence of the detecting substance. The term "sample" refers to a sample from the subject including a cell, for example, urine, serum, blood, plasma, saliva, sputum, feces, tear, hair, nails, and organ tissue, and other samples including a cell from the subject.

In some embodiments the cells that comprise the sample are brain cells. In some embodiments the samples include neuron cells. In this regard, the detecting substance can be calcium, which plays a role in neuronal signaling. Thus, the present methods can utilize the isolated polypeptides to label "active" cells during a particular stimulus, and quantify and characterize calcium activity in response to that stimulus. Similarly, the present methods can be used to trace neurons based on their calcium activity. Those of ordinary skill will appreciate further uses for detecting methods that utilize the present isolated polypeptides.

There are various ways that the isolated polypeptide can be made to contact a sample. In some embodiments the isolated polypeptide is injected directly or via a carrier to a particular site that includes the cells that are to be observed. In other embodiments the isolated polypeptide is transgenically delivered to cells that comprise a sample. The term "transgenic" and the like is used herein to refer to introducing particular genetic material into the genome of a cell or organism. Thus, cells that have had the gene for the isolated polypeptide for the isolated polypeptide transgenically delivered to the cells can express the isolated polypeptide themselves.

With regard to the exposing step, a sample may be exposed to any type of light and for any duration that induces a change in fluorescence of the isolated polypeptide. In color-changing photoconvertible polypeptides, exposure to light will induce a color shift in the polypeptides that can be dependent on the concentration of a detecting substance in the sample. The duration of time that a sample is exposed is not particularly limited. In some embodiments light is exposed for a time period sufficient to expose the cells within a particular volume of sample. In specific embodiments the light for exposing a sample can be emitted for a time period of about 1 millisecond, 1 second, 10 seconds, 20 seconds, 30 seconds, 40 seconds, 50 seconds, 60 seconds, 1 minute, 2 minutes, 3 minutes, 4 minutes, 5 minutes, 6 minutes, 7 minutes, 8 minutes, 9 minutes, or 10 minutes. In other embodiments the light for exposing a sample can be emitted for a time period of about 0.5 hours, 1 hour, 2 hours, 3 hours, 4 hours, 5 hours, or more.

The type of light that is used to expose a sample is generally only limited in that it should comprise a wavelength that can stimulate a particular photoconversion, photoactivation, or the like. The term "light" refers to any electromagnetic radiation including, but not limited to, visible light, microwave light, ultraviolet light, or the like. The light can have a wavelength of about 100 nm, about 200 nm, about 300 nm, about 400 nm, about 500 nm, about 600 nm, about 700 nm, about 800 nm, about 900 nm, or about 1000 nm. The light may also have a wavelength falling either above or below these recited wavelengths so long as it can induce a photoconversion or photoactivation in the isolated polypeptide.

Once the sample with the isolated polypeptide has been exposed to light, one can detect the presence of a detecting substance in the sample. The presence of a detecting substance can be evidenced by a color shift of the fluorescence emitted by the isolated polypeptide. The presence of a detecting substance can also be evidenced by a change in the intensity of a fluorescence emitted by an isolated polypeptide. Thus, the presence and/or degree of a change in fluorescence of an isolated polypeptide can be indicative of the presence and/or concentration of a detecting substance in a sample.

In this regard, in some embodiments the presence of a detecting substance can be measured by observing the extent of the color shift in an isolated polypeptide. In some embodiments the greater the extent of the color shift the higher the concentration of the detecting substance in the sample. For instance, with a green-to-red isolated polypeptide that can detect calcium, the isolated polypeptide will display a higher percentage and/or amount of red fluorescence as the concentration of calcium increases. Furthermore, in some embodiments of the present methods that utilize isolated polypeptides that shift from a first color to a second color, the presence of a detecting substance can be measured by observing a change in a ratio of the second color to the first color. The higher the ratio of the second color to the first color, the higher the relative concentration of the detecting substance. Utilizing a ratio to detect the presence of detecting substance can be advantageous since the method is mostly if not entirely independent of expression level rather than the total concentration of a detecting substance.

In some embodiments the fluorescence color or intensity change experienced by an isolated polypeptide that has contacted a detecting substance and has been exposed to light can be permanent or nearly-permanent. The term nearly-permanent refers to a change that lasts for a time period sufficient to allow for analysis of a sample outside of just one field of view (e.g., of a standard microscope performing live imaging), thereby permitting a user to scan an area that is greater than a field of view to quantify and characterize the presence of a detecting substance. This permits the measure of activity over relatively larger areas of tissue, does not require real-time imaging, and permits measurement to be conducted after preparing tissues by, for example, fixing or sectioning tissues.

In some embodiments the isolated polypeptides thus function as an integrator of a detecting substance. The integrators detect the presence of, and particular concentration increases, a detecting substance in a sample. In this regard, the term "integrator" as used herein refers to compounds having signals that permanently or substantially permanently increase over time, as they are exposed to light, at a rate that is dependent on the concentration of a detecting substance. Integrators can exhibit an increasing signal over time even though the concentration of a detecting substance may fluctuate up and down. Alternatively, integrators may act in a negative fashion, showing increasing signal in the absence of the detecting substance or cellular state.

Exemplary isolated polypeptides can also function as an indicator. In some embodiments the isolated polypeptides are indicators of a detecting substance that can indicate whether a sample currently has a particular detecting substance. In this regard, the term "indicator" as used herein refers to compounds that exhibit a signal that is dependent on the concentration of a detecting substance, wherein the signal fluctuates in accordance with fluctuations in concentration of the detecting substance.

In some embodiments the isolated polypeptides function as both integrators and as indicators of a detecting substance.

Accordingly, the presently-disclosed subject matter includes methods of using the isolated polypeptides as described herein as a reporter for ion activity, as a sensor for an analyte, as an agent for imaging experiments, as a measure of the effect of small molecule pharmaceutical candidates on target protein and/or cellular and/or organismal activity, and the like. The presently-disclosed subject matter further includes a method of producing an isolated polypeptide or nucleic acid molecule as described herein, using the methods and schemes as set forth in the Examples and Figures, for example.

EXAMPLES

The presently-disclosed subject matter is further illustrated by the non-limited examples set forth below. The examples may include compilations of data that are representative of data gathered at various times during the course of development and experimentation related to the presently-disclosed subject matter.

Example 1

This Example describes procedures used to design and synthesize novel fluorescent proteins. This Example further describes procedures used to optimize and characterize the novel fluorescent proteins.

Circular permutation of fluorescent protein domains and attachment to ligand binding domains can allow modulation of fluorescence intensity through conformational rearrangement of a FP chromophore chemical environment driven by ligand binding. Thus, the procedures described herein utilized a circular permutation of a photoconvertible fluorescent protein, EosFP, to attempt to permit modulation of photoconversion efficiency of the protein in a ligand-dependent manner.

To construct a fluorescent protein that would undergo more efficient green-to-red photoconversion in the presence of calcium, libraries were created and screened for circularly permuted EosFP variants fused at the termini to calmodulin (CaM) and the calmodulin-interacting peptide M13. Circularly permuted variants of mEos2 were generated carrying the additional mutations V2ins, F34Y, S39T, A69V, L93M, and I102Y by PCR amplification from a template comprising tandem copies of the variant Eos gene separated by a linker encoding GGTGGS SEQ ID NO: 13. The first copy of the variant Eos gene lacked a stop codon. The PCR reaction included five forward primers and five reverse primers to allow variation in the position/length of each terminus, yielding 25 distinct combinations of termini. Each primer additionally contained one NNS variable codon to allow variation in amino acid sidechain at each FP terminus. PCR products were ligated between M13-CaM or CaM-M13, yielding a total theoretical library size of 20,000. Eleven such libraries were created, centered on the middle of each of the eleven beta strands of Eos.

To screen for calcium-modulated photoconversion, libraries were transformed into T7 Express *E. coli* (NEB) and colonies were grown overnight at 37° C. The colonies that were visibly green fluorescent under a stereomicroscope after additional incubation for 48 hours at 4° C. were placed into 1 mL of autoinduction media in 96-well blocks. Cultures were grown at 30° C. for 36 h, harvested by centrifugation, and the cell pellets frozen at −20° C. Cell pellets were thawed and resuspended in 500 uL of lysis buffer (100 mM MOPS, 100 mM KCl, 1 mg/mL lysozyme) and were shaken at 30° C. for 1 h to allow cell lysis. Cell debris was pelleted by centrifugation at 6100×g and 95 µL of each lysate was transferred to two separate 96-well microplates and mixed with calcium chloride and EGTA, respectively, to final concentrations of 0.5 mM and 1 mM. Green and red fluorescence was measured in a plate reader (Tecan, Mannedorf, Switzerland), followed by illumination with a 405 nm LED array (~200 mW/cm$^2$, Loctite, Dusseldorf, Germany) for 80 s and another measurement of green and red fluorescence was taken. Finally, the +/− calcium plates were switched by adding EGTA to 10 mM in the original calcium plate, and CaCl$_2$ was added to 5 mM in the original EGTA plate. The green and red fluorescence was measured again.

For each library variant, the fluorescence change +/− calcium in both the green and red channels as well as the difference in the extent of photoconversion +/− calcium were calculated using the following formula:

$$\frac{\Delta R}{R_0} = \frac{\frac{F_R^{Ca^{2+}}}{F_G^{Ca^{2+}}} - \frac{F_R^{EGTA}}{F_G^{EGTA}}}{\operatorname{Min}\left(\frac{F_R^{Ca^{2+}}}{F_G^{Ca^{2+}}}, \frac{F_R^{EGTA}}{F_G^{EGTA}}\right)}$$

Up to 3,200 fluorescent clones were screened per library. Libraries within beta strands 1, 5, 7, 8, 9 of EosFP exhibited a significant number of fluorescent colonies. Individual library clones exhibited up to 5-fold more photoconversion in the presence of calcium (strand 7 library, CaM-M13 topology), or nearly 6-fold more photoconversion in the absence of calcium (strand 7 library, M13-CaM topology). The top three clones that photoconverted faster in the presence of calcium had identical sequences. These sequences were referred to as Calcium-Modulated Photoactivatable Ratiometric Integrator (CaMPARI).

Next, a small amount of protein was expressed and purified to measure fluorescence brightness and calcium affinity. The variant exhibiting the best photoconversion contrast +/− calcium, maintained a reasonable fluorescence brightness, and exhibited reasonable calcium affinity was selected for optimization (CaMPARI v0.1). CaMPARI v0.1 photoconverted 5-fold faster with calcium, and was pursued because many biological signaling events result in increased calcium. The signal in this case (i.e., red-to-green ratio) increased from zero to produce a higher signal-to-noise ratio (SNR). (SEQ ID NO: 12).

Optimization was carried out by saturation mutagenesis using the Quikchange multi-site methodology (Agilent, Santa Clara, Calif.) with NNS codons at individual codon positions within the EosFP domain and the M13 domain. Screening of each 96-clone library was done with the *E. coli* lysate assay described above. In a second round of optimization, combinations of beneficial single amino acid variants were generated in a small library and screened in the same manner.

Accordingly, by screening libraries of variants at individual codon positions, variants were identified that improved the fluorescence brightness and/or photoconversion rate difference +/− calcium. Several of these variants were combined to produce CaMPARI v1 (SEQ ID NO: 1).

Example 2

This Example describes procedures used to determine the crystal structure of the novel fluorescent proteins. The crystal structures of this Example were used to, among other things, identify mutations that may enhance the properties of the fluorescent proteins.

To develop a crystal structure, purified CaMPARI v0.2 (CaMPARI v0.1 with E380M mutation) protein in 10 mM Tris, 100 mM NaCl, 10 mM EGTA was mixed with an equal volume of a precipitant solution of 200 mM ammonium sulfate, 100 mM HEPES pH 7.5, 25% PEG 3350 at room temperature in a sitting-drop vapor diffusion setup. A single yellow-green dagger-shaped crystal was cryoprotected in the precipitant solution supplemented with 20% glycerol, and x-ray diffraction data were collected at 100 K. Data were processed using MOSFLM and SCALA within the CCP4 software package. The structure was solved by molecular replacement searching first for the EosFP fragment using a single EosFP molecule from PDB ID 1ZUX, followed by portions of the CaM domain using a fragment of PDB ID 3EKJ. Iterative model building and refinement led to the model described in Table 1.

The resulting crystal structure of CaMPARI v0.2 in the absence of calcium includes circularly permuted EosFP (cpEos), CaM, and M13 domains as well as interfaces between the domains. This information was used to help target mutagenic libraries for optimization of CaMPARI properties, as described in Example 1.

TABLE 1

X-ray crystallographic data collection and refinement statistics.

| Data Collection | |
| --- | --- |
| Crystal | CaMPARI v0.2 apo |
| Space Group | P4$_1$2$_1$2 |
| Unit Cell Dimensions | |
| a (Å) | 68.7 |
| b (Å) | 68.7 |
| c (Å) | 172.8 |
| X-ray source | ALS 8.2.2 |
| Temperature (K) | 100 |
| Wavelength (Å) | 1.000 |
| Resolution Range (Å) | 69-2.0 |
| Completeness (%) | 99.9 (99.5) |
| Redundancy | 7.5 (6.6) |
| I/σ(I) | 13.4 (4.0) |
| R$_{sym}$ (%) | 9.4 (51.2) |
| Refinement | |
| R$_{cryst}$/R$_{free}$ (%) | 19.2/23.0 |
| Resolution Range (Å) | 54-2.0 |

Numbers in parentheses are for the highest resolution shell data.

Example 3

This Example describes procedures performed to characterize the in vitro properties of the fluorescent proteins. First, CaMPARI protein was expressed from the pRSET plasmid (Life Technologies, Carlsbad, Calif.) in T7 Express E. coli cells cultured for 36 h in 100 mL of autoinduction medium supplemented with 100 mg/L ampicillin. Cell pellets were lysed using B-PER (Pierce, Rockford, Ill.) supplemented with 1 mg/mL lysozyme and 1 minute of sonication. After removing insoluble material by centrifugation, CaMPARI protein was purified by immobilized metal affinity chromatograpy on nickel-charged Profinity resin (Bio-Rad, Hercules, Calif.), washing with 10 mM imidazole, and eluting with 100 mM imidazole.

Protein concentration was quantitated by denaturing in 0.1 M NaOH and using the extinction coefficient 44,000 M$^{-1}$ cm$^{-1}$ at 447 nm for denatured GFP-like chromophores. Quantum yields were measured directly with an integrating-sphere spectrometer (Quantaurus-QY, Hamamatsu, Japan).

Using these samples, calcium titrations were used to calculate an apparent affinity of the protein for calcium ions. Aliquots of purified CaMPARI protein were mixed with Ca-EGTA solutions calculated to contain a range of free Ca$^{2+}$ ions (Life Technologies) and fluorescence was measured in a plate reader. Sigmoidal fits to the titration data in Prism (Graphpad, La Jolla, Calif.) were used to estimate the dissociation constant (Kd) and the Hill coefficient for each variant.

Furthermore, to observe the photoconversion rate difference +/− calcium, purified CaMPARI in 5 mM CaCl$_2$ or 5 mM EGTA were photoconverted using a 405 nm LED array with an intensity of 200 mW/cm$^2$ (Loctite). Green and red fluorescence was measured at various time points to fit an exponential rate to the appearance of red fluorescence or the disappearance of green fluorescence.

The rate of fluorescence decrease accompanying calcium unbinding (k$_{off}$) was determined from a single exponential fit to the fluorescence decay following rapid mixing of purified protein samples in 1 μM calcium with a solution of 10 mM EGTA at room temperature, both buffered with 50 mM MOPS, 100 mM KCl at pH 7.2, using a stopped-flow device (Applied Photophysics) coupled to a fluorometer (Varian).

Chromophore pK$_a$ values were obtained by diluting purified proteins into pH buffers containing 50 mM citrate, 50 mM Tris, 50 mM glycine, 100 mM NaCl, and either 5 mM CaCl$_2$ or 5 mM EGTA that were adjusted to twelve different pH values between 4.5 and 10.5. pK$_a$ values were determined from the inflection point of a sigmoid fit to fluorescence versus pH.

Figure 1B:
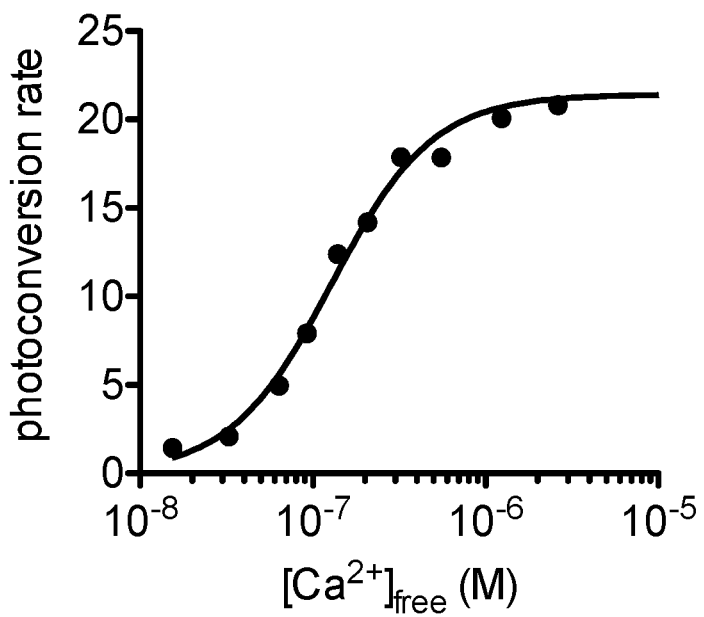
Figure 2:
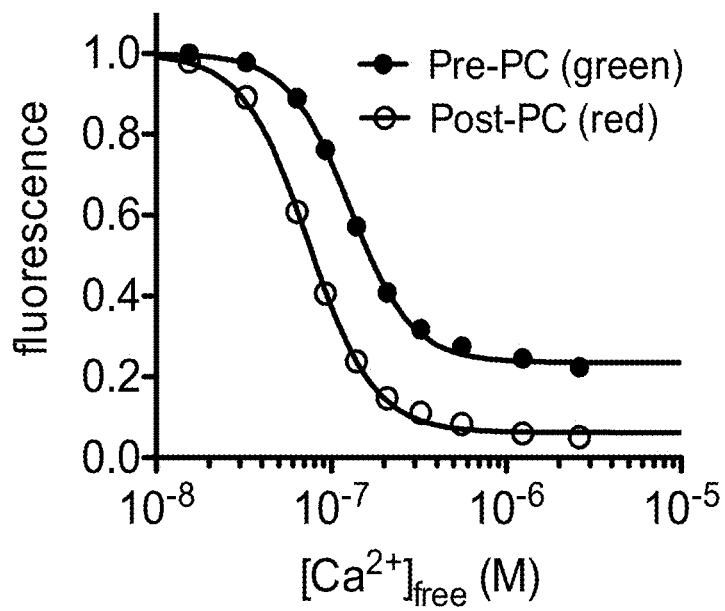
FIG. 2 includes a plot showing the amount of green or red fluorescence for purified CaMPARI protein before photoconversion (Pre-PC) or after photoconversion (Post-PC) as a function of $Ca^{2+}$ concentration in buffer solution. A sigmoidal binding curve was fit to the data to estimate calcium dissociation constants ($K_d$).
Figure 3A:
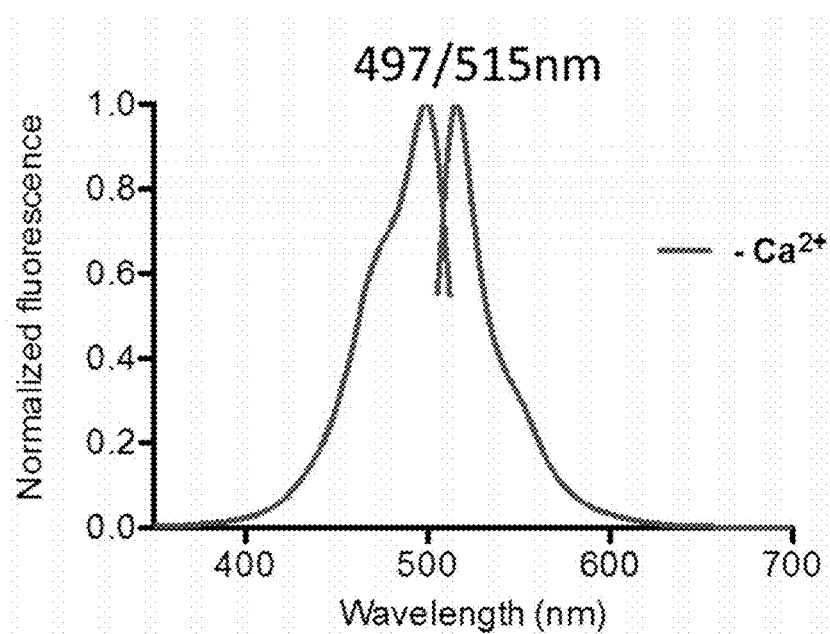
FIGS. 3A to 3D include plots showing the fluorescence (A,C) and absorbance (B,D) spectra of purified CaMPARI protein solutions either in the absence of calcium (solid traces) or in the presence of 5 mM calcium (dashed traces), where spectra are shown before any exposure to photoconversion light (A,B) and after extensive exposure to photoconversion light (C,D) (fluorescence excitation and emission maxima indicated in (A,C)).
Figure 3B:
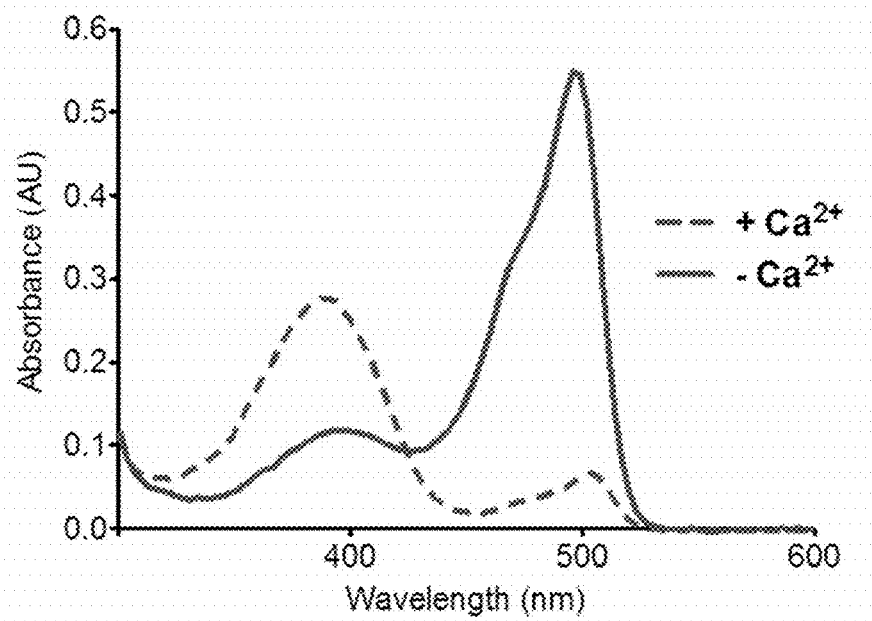
Figure 3C:
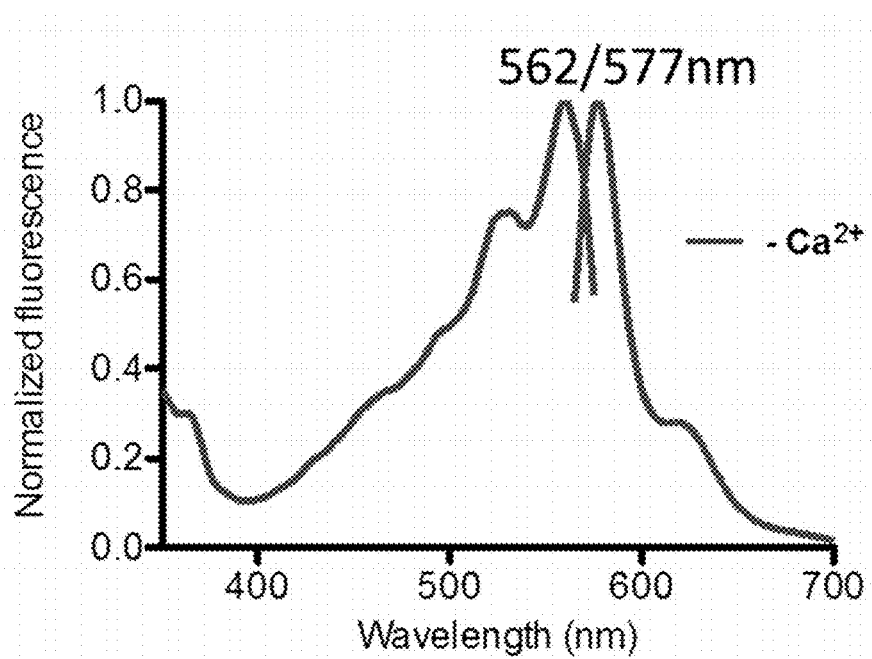
Figure 3D:
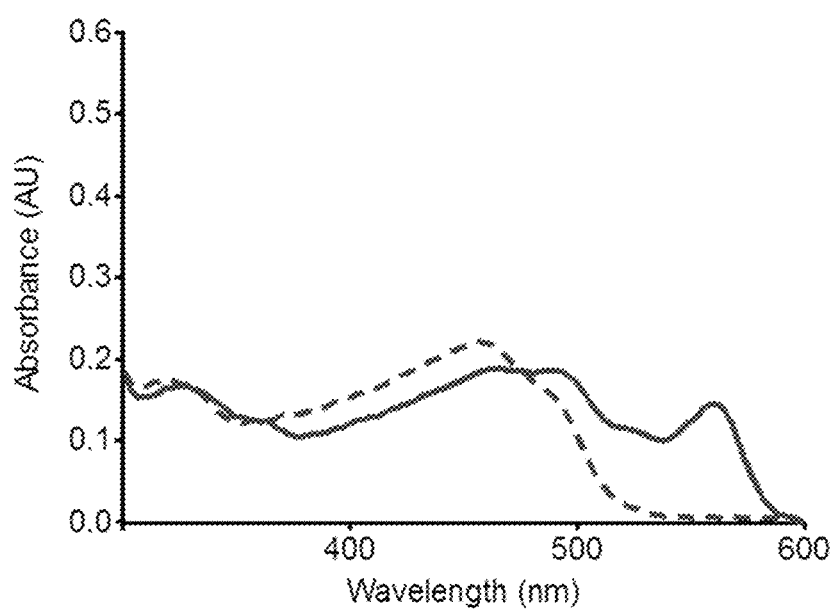

It was observed that purified CaMPARI v1 protein (hereinafter simply referred to as "CaMPARI") comprised a 29-fold faster green-to-red photoconversion rate in the presence of calcium (FIGS. 1A and 1B). The green and red forms of CaMPARI were 8-fold and 34-fold less fluorescent, respectively, in the presence of calcium. The fluorescence change with increasing calcium was used to estimate a dissociation constant (K$_d$) of 130 nM (FIG. 2). Addition of the nuclear export signal (NES) MLQNELALKLAGLDIN-KTG SEQ ID NO: 6 to the N-terminus increased the affinity for calcium, with K$_d$=106 nM. The fluorescence excitation and emission spectra were similar to EosFP (FIG. 3).

Example 4

This Example describes procedures used to characterize how the novel fluorescent proteins respond in histamine-stimulated HeLa cells. It is known that, in response to extracellular exposure to micromolar concentrations of histamine, HeLa cells undergo large cytoplasmic calcium oscillations. Thus, this Example describes how the novel fluorescent proteins can detect and characterize cytoplasmic calcium oscillations.

HeLa cells were nucleofected with plasmids allowing expression of CaMPARI and plated on glass-bottom dishes. 48 h after nucleofection, CaMPARI-expressing HeLa cells were washed three times with HBSS containing 20 mM MOPS, pH 7.2. Histamine was then added and green fluorescence was imaged at 1 Hz using a 20× objective on an inverted epifluorescence microscope. A 1 s pulse of photoconversion light (4.2 W/cm$^2$) was delivered through the 20× objective about four minutes after addition of histamine. After photoconversion, the buffer was changed to HBSS with 20 mM MOPS, 10 mM EGTA, pH 7.2 to deplete intracellular calcium, and the green and red fluorescence was then imaged after photoconversion. All epifluorescence imaging and photoconversion in HeLa cells and cultured neurons was done using a mercury lamp with the following filter combinations. Green fluorescence:excitation=475/23 nm, dichroic mirror=495 nm, emission=511/20 nm; red fluorescence:excitation=555/20 nm, dichroic mirror=561 nm, emission=612/69 nm; photoconversion:excitation=440 nm/SP, dichroic mirror=580 nm. Cytoplasmic regions of HeLa cells were manually segmented (ImageJ, http://imagej.nih.gov/ij/) for calculation of the green fluorescence time-course and the final red and green intensities.

It was observed that addition of 1 μM histamine to HeLa cells expressing CaMPARI induced periodic, transient decreases in green fluorescence from the cells, consistent with the observed decreased fluorescence of the purified protein upon addition of calcium. Exposure to a 2 s pulse (4 W/cm$^2$) of photoconversion light during histamine-induced calcium oscillations followed by imaging of the cells in the red and green fluorescence channels after removal of calcium with ionomycin/EGTA revealed a wide range in the extent of photoconversion, seen in either the composite image of red and green fluorescence or the red/green ratio. The extent of photoconversion in each HeLa cell correlated with the green fluorescence brightness (i.e., intracellular calcium concentration) immediately prior to the photoconversion pulse. Cells that were near the peak of a calcium oscillation underwent more green-to-red photoconversion and appeared more red, while cells that were closer to the low baseline intracellular calcium concentration photoconverted less and appeared more green.

Example 5

This Example describes procedures conducted on cultured rat hippocampal neurons and that are intended to further characterize the novel fluorescent proteins. In particular, this Example describes the response of the proteins in cultured neurons to electric field-stimulations as well as the effects that fixation have on the proteins' fluorescent signals.

First, cultured rat hippocampal neurons were prepared and infected with lentivirus or AAV particles encoding CaMPARI from the human synapsin promoter starting four days after isolation. The neurons were imaged ten days after infection with a 10× objective on a widefield fluorescence microscope (IX-81, Olympus) before and after various combinations of photoconversion and field electrode-induced action potential firing, which were controlled by custom scripts in MetaMorph (version 7.7.5, Molecular Devices) and Ephus (ephus.org). Prior to imaging, the neuron cultures were washed with imaging buffer (145 mM NaCl, 2.5 mM KCl, 10 mM glucose, 10 mM HEPES, pH 7.4, 2 mM $CaCl_2$, 1 mM $MgCl_2$) and spontaneous synaptic activity was blocked with a drug mix (10 mM CNQX, 10 mM (R)-CPP, 10 mM gabazine, 1 mM (S)-MCPG, Tocris Bioscience). Segmentation of neurons was done using a threshold in the green fluorescence channel (ImageJ) prior to any photoconversion or electrical stimulation.

Figure 4A:
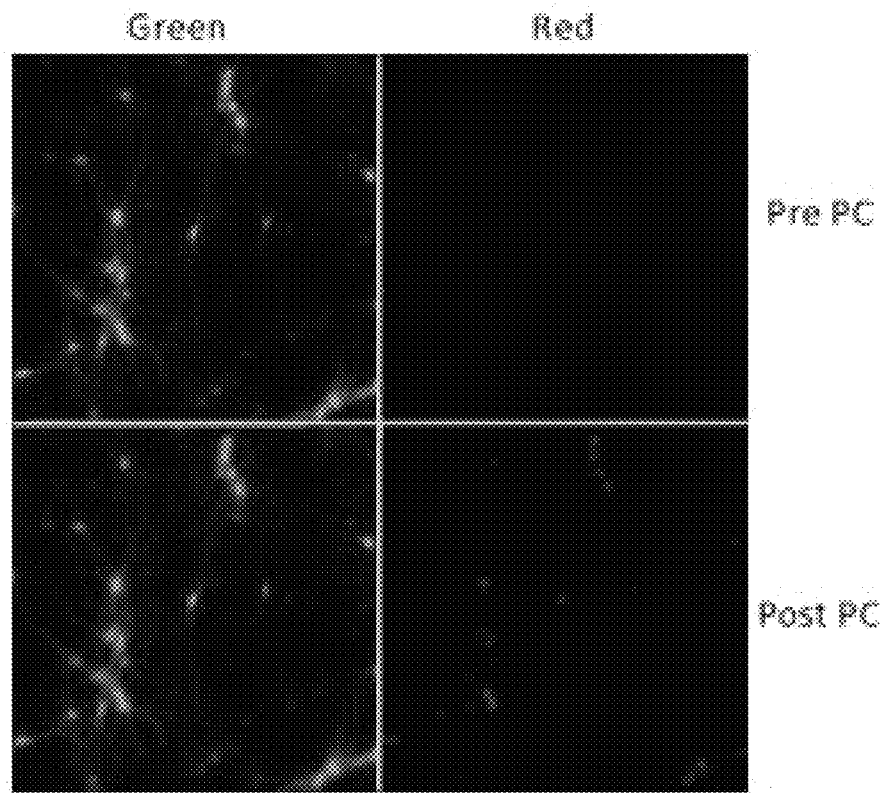
FIGS. 4A and 4B include images showing (A) cultured rat hippocampal neurons expressing CaMPARI both before (top) and after (bottom) exposure to 2 s of photoconversion light, and (B) same as panel (A) with the addition of 80 Hz field stimulation.
Figure 4B:
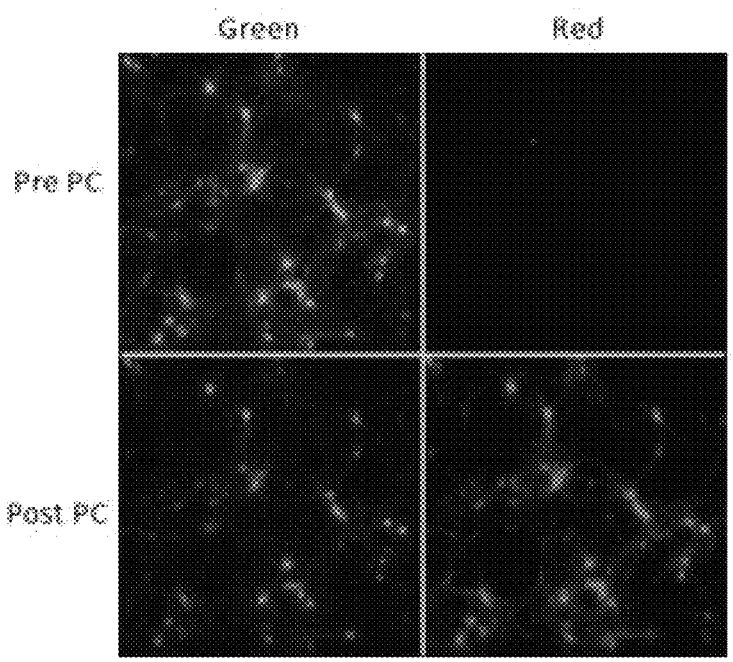
Figure 5A:
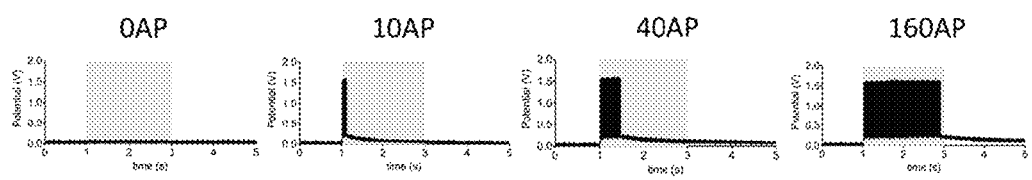
FIGS. 5A to 5C include plots and images showing (A) a protocol for exposing cultured rat hippocampal neurons expressing CaMPARI to 2 s photoconversion light pulses (shaded box) accompanied by 83 Hz action potential (AP) trains of different lengths (black traces), (B) the red/green ratio of the neuron fluorescence imaged after the various photoconversion/field stimulation pulses shown in (A), and (C) a quantification of the red/green signal within neurons following the various photoconversion/field stimulation pulses shown in (A), normalized to the response at 0 AP, for both CaMPARI and the parent EosFP variant control.
Figure 5B:
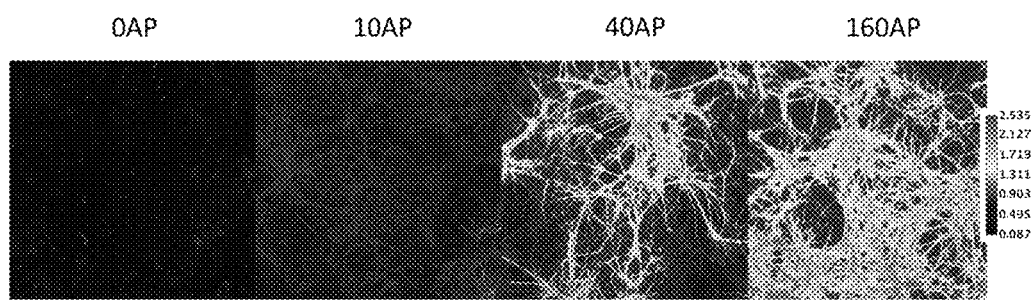
Figure 5C:
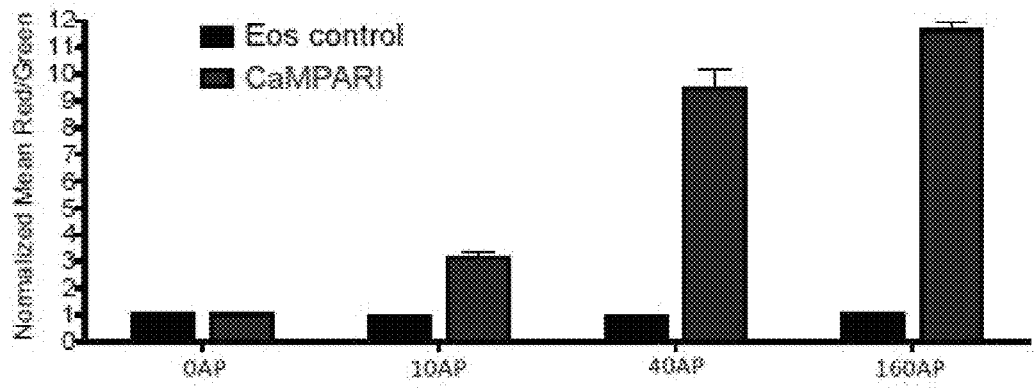
Figure 6A:
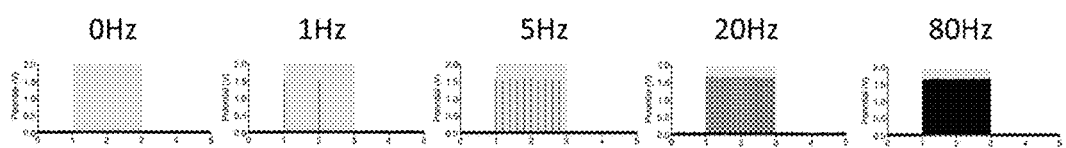
FIGS. 6A to 6C include plots and images showing (A) a protocol for exposing cultured rat hippocampal neurons expressing CaMPARI were exposed to 2 s photoconversion light pulses (shaded box) accompanied by action potential (AP) trains of different frequencies (black traces), (B) the red/green ratio images of the neuron fluorescence imaged after the various photoconversion/field stimulation pulses shown in (A), and (C) a quantification of the red/green signal within neurons following the various photoconversion/field stimulation pulses shown in (A), normalized to the response at 0 Hz.
Figure 6B:
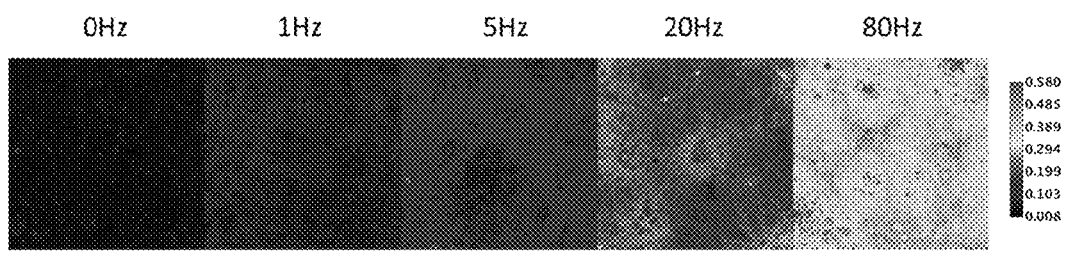
Figure 6C:
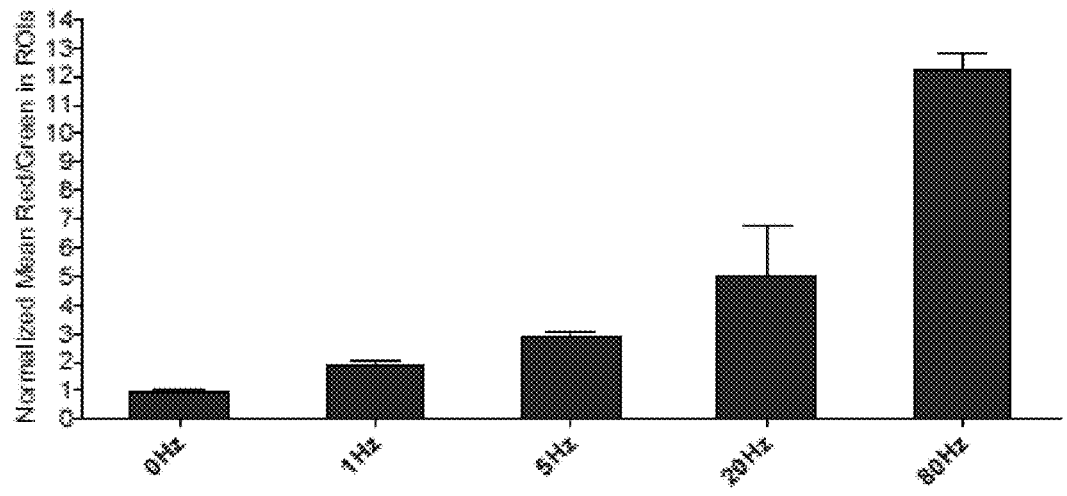
Figure 7A:
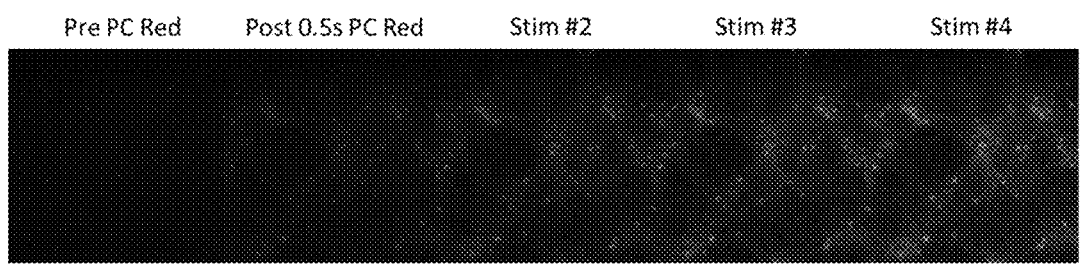
FIGS. 7A and 7B include (A) images showing the red fluorescence acquired after exposing cultured rat hippocampal neurons expressing CaMPARI to each of four consecutive pulses of 0.5 s of photoconversion light accompanied by 80 Hz field stimulation, and (B) a plot showing the red/green ratio in neurons following each light pulse accompanied by either no field stimulation or 80 Hz field stimulation (left Y-axis, two left bars) and the ratio of 80 Hz/0 Hz signal after each pulse (right Y-axis, right bar).
Figure 7B:
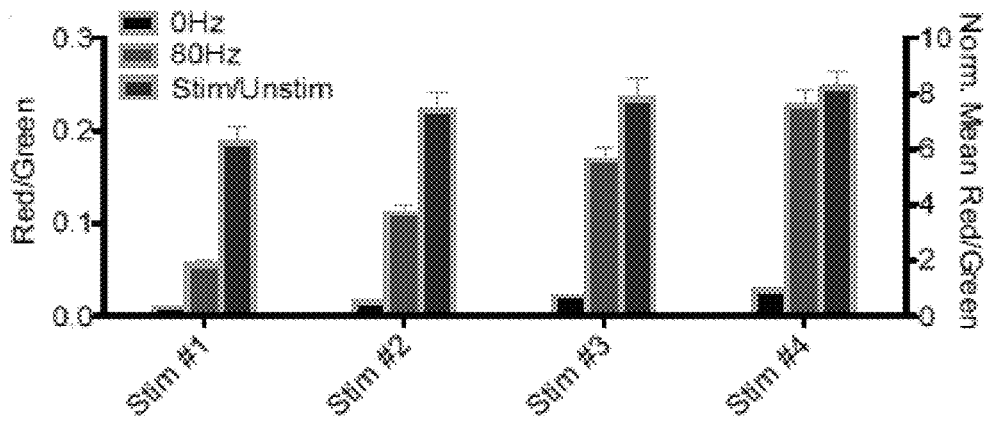
Figure 8:
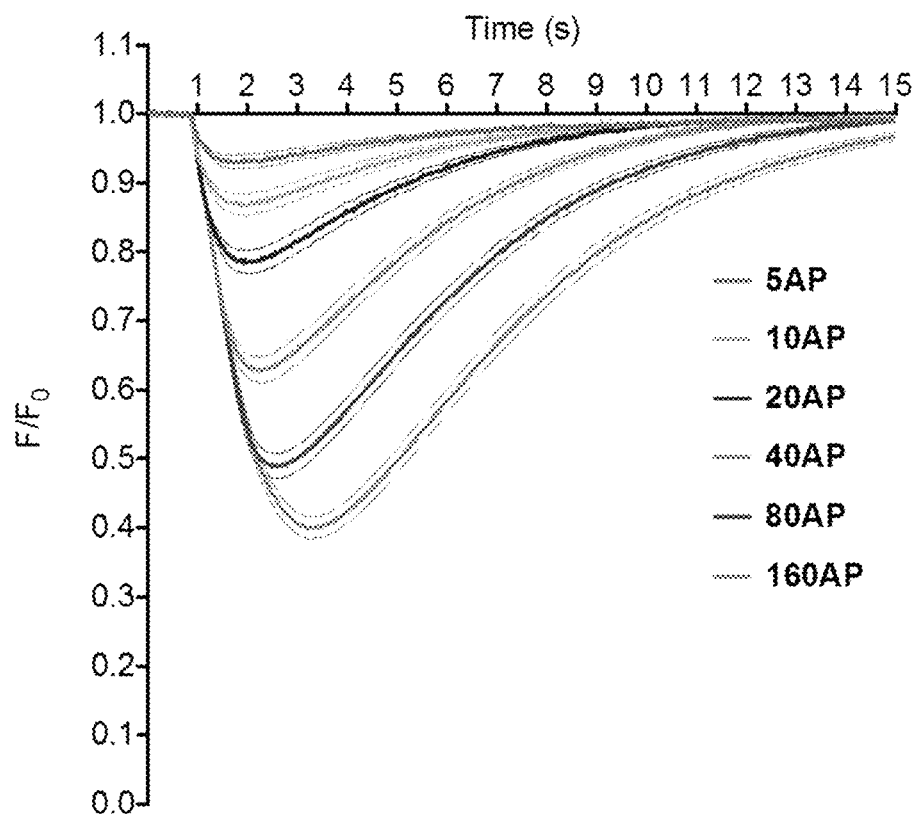
FIG. 8 includes a plot showing the average and standard deviation green fluorescence after exposing cultured rat hippocampal neurons expressing CaMPARI to 83 Hz action potential (AP) trains of different lengths induced by field stimulation during simultaneous epifluorescence imaging of the green fluorescence signal (F, fluorescence at a given time; $F_0$, fluorescence during the 1 s prior to field stimulation).

The imaging showed that the CaMPARI expressed in primary rat hippocampal neurons in culture exhibited bright green fluorescence (FIG. 4) and did not exhibit visible red fluorescence. Following a 2 s pulse of photoconversion light (1.5 W/cm$^2$) to CaMPARI-expressing neurons, there was no significant decrease in green fluorescence and a small amount of red fluorescence was visible (FIG. 4A). Following application of the same dose of photoconversion light concurrent with field electrode stimulation of the neurons to induce action potential firing at 80 Hz, a significant decrease in green fluorescence and a bright red signal was observed in the neurons (FIG. 4B). Stimulation of 0, 10, 40, or 160 action potentials (83 Hz) at the beginning of a 2 s photoconversion pulse (FIG. 5A) produced increasing amounts of green-to-red photoconversion (FIG. 5B), up to 12-fold more for 160 action potentials relative to 0 (FIG. 5C). No effect of field electrode stimulation on photoconversion was observed for the parent EosFP variant (FIG. 5C). Similarly, increasing frequencies of field electrode stimulation during photoconversion light exposure (FIG. 6A) produced increasing amounts of green-to-red photoconversion (FIGS. 6B and 6C). Repeated exposures of CaMPARI-expressing neurons to shorter photoconversion light pulses (0.5 s) led to increasing amounts of red fluorescence signal (FIG. 7A) and red/green ratio (two left bars in FIG. 7B), but the ratio of red-to-green photoconversion between 80 Hz field stimulated and unstimulated neurons remained approximately constant (right-most bars in FIG. 7B). Field electrode stimulation of CaMPARI-expressing neurons (without application of photoconversion light) led to transient decreases in the green fluorescence signal, proportional to the number of induced action potentials (FIG. 8).

Also, as stated above, the fluorescent signals were observed after fixing the neurons, particularly since fixation can also alter the signals of fluorescent compounds after photoconversion and prior to imaging. Of course, cell or tissue fixation protocols are often used to halt physiological processes in cells, such as protein translation or degradation, and to allow antibody staining of cells.

Figure 9A:
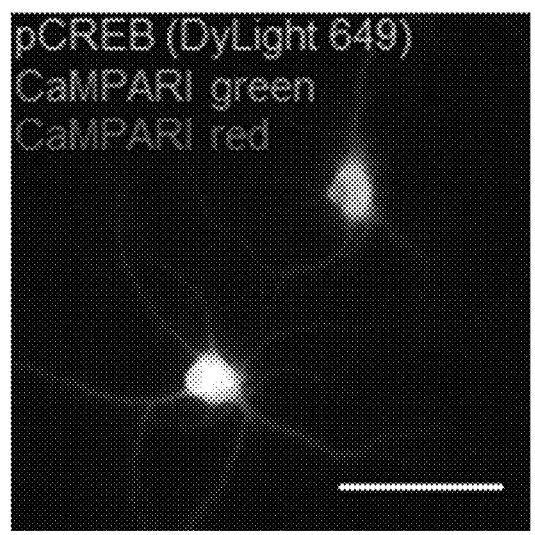
FIGS. 9A to 9C include data for the in vitro characterization of CaMPARI, showing (A) a composite widefield fluorescence micrograph from one field of view containing two fixed, immunostained neurons, one expressing an ATP-gated calcium channel (P2X) and one that did not, (B) individual color channels from the same field of view as (A), and (C) a plot of intensity of phospho-CREB staining and CaMPARI photoconversion for high potassium depolarization (90 mM K$^+$), controls (4 mM K$^+$), and pharmacogenetic activation of a subset of P2X-expressing neurons with 100 µM ATP.
Figure 9B:
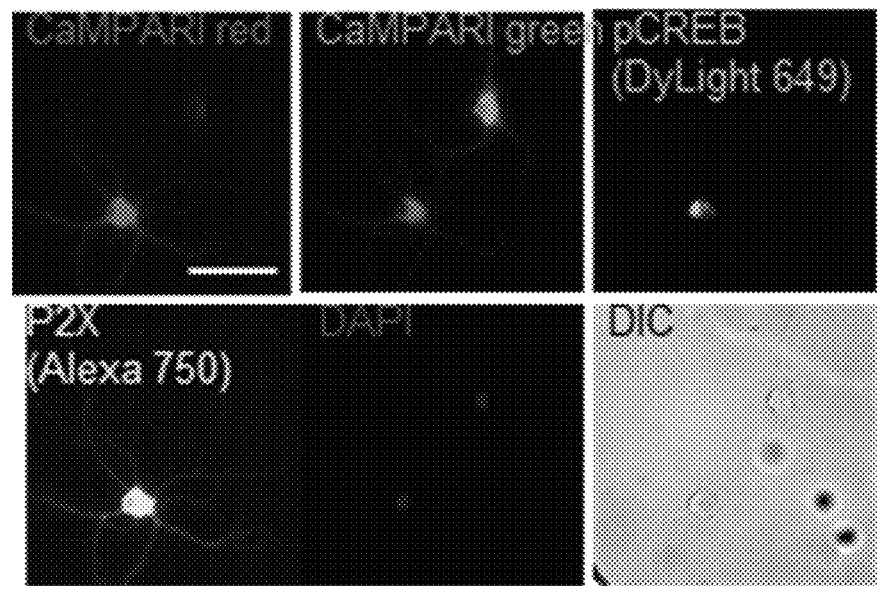
Figure 9C:
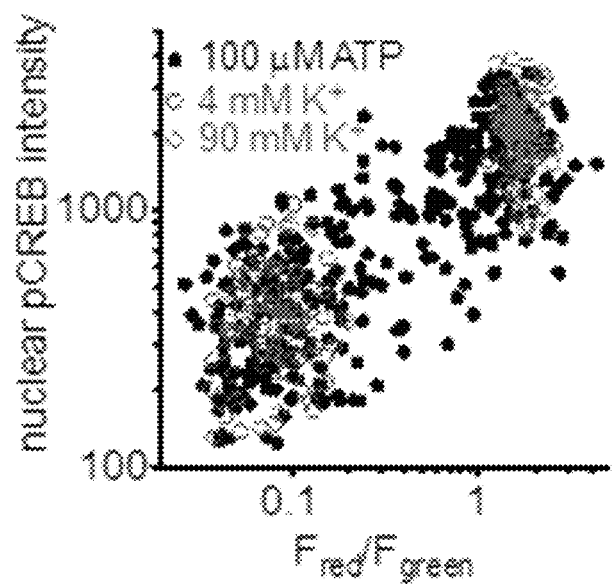

To test the CaMPARI samples, cultured rat hippocampal neurons expressing CaMPARI were depolarized either by elevating extracellular potassium or via pharmacogenetic activation of exogenously expressed P2X channels, both in concert with photoconversion. Cells were fixed with 4% paraformaldehyde (PFA) and co-labeled using traditional antibody staining techniques, providing five simultaneous color channels of information (2 colors for CaMPARI+3 additional channels) (FIGS. 9A and 9B). The green and red fluorescence of CaMPARI each decreased by about 50% upon PFA fixation. The retention of CaMPARI photoconversion signal through fixation, permeabilization, and multicolor antibody labeling enabled [$Ca^{2+}$] levels within individual cells to be directly correlated to independent proteomic metrics typically used for post hoc inference of neural activity. Fixed neurons were co-immunolabeled for P2X expression level, and phosphorylated nuclear cAMP-responsive element-binding protein (pCREB), which increased with elevated intracellular calcium (FIG. 9C). Thus even after chemical fixation, ratiometric CaMPARI signal remains a reliable readout of activity, consistent with conventional immunofluorescence and in situ hybridization markers.

Example 6

This Example describes procedures used to characterize the novel fluorescent proteins in vivo. In particular, this Example describes properties of CaMPARI that has been transgenically delivered to a mouse and is expressed in the cortical neurons.

To transgenically deliver CaMPARI, a pregnant mouse (E16) was deeply anesthetized with isoflurane (2%). Then, the uterine horns were surgically exposed and plasmid DNA (5 mg/ml) mixed with 0.03% Fast Green dye in phosphate buffer was injected into the ventricle of embryos through a micropipette (~0.1 µL per embryo). Electroporation was done using custom forceps electrodes (5 pulses, 100 ms, 40 V). Additionally, 30 nL volumes of adeno-associated virus (AAV) particles in saline solution were stereotactically injected into the V1 region of another anesthetized mouse's visual cortex through the thinned skull of the mouse.

Imaging was done with a custom-built two-photon microscope with a resonant scanner. The excitation source was a Mai Tai HP 100 femtosecond-pulse laser (Spectra-Physics) running at 1000 nm. The objective lens was a 16× dipping lens with 0.8 NA (Nikon). Emission filters were Chroma ET525/50 and ET600/60 for CaMPARI green and red, respectively. Images were collected at 15 Hz.

Figure 10A:
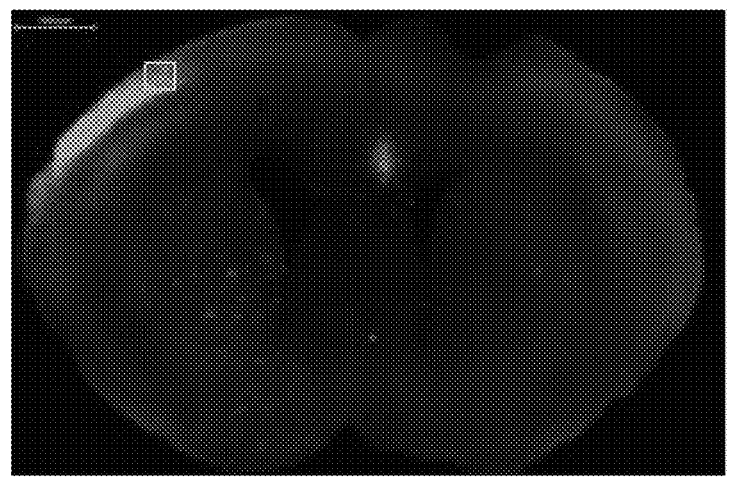
FIGS. 10A to 10E include images showing (A) a slide scanner image of green fluorescence from CaMPARI in a fixed 50 µM slice of mouse brain expressing CaMPARI from the CAG promoter two weeks after birth following in utero electroporation at E16, (B) a green fluorescence confocal microscopy image of the boxed region in (A) showing cell bodies of layer 2/3 cortical neurons and processes, (C) a higher magnification green fluorescence confocal microscopy image of layer 2/3 cortical cell bodies, (D) a portion of a labeled axon with bouton structures, and (E) a portion of a labeled dendrite with spine structures.
Figure 10B:
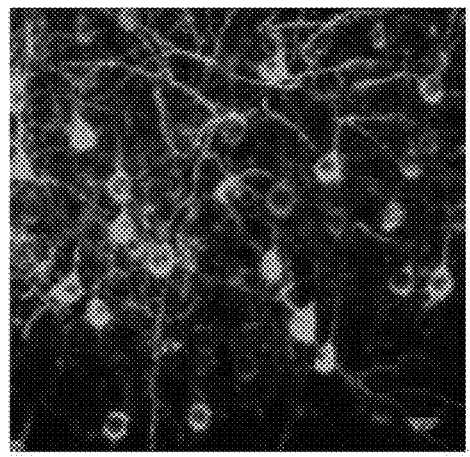
Figure 10C:
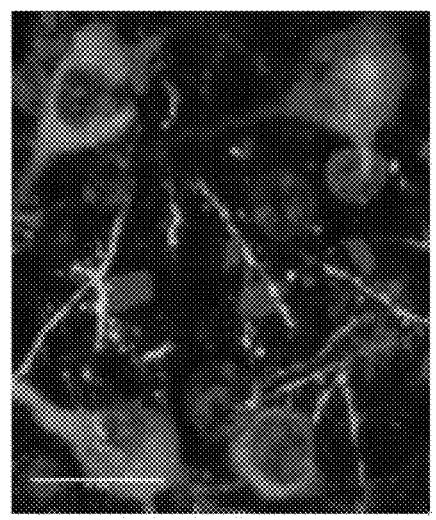
Figure 10D:
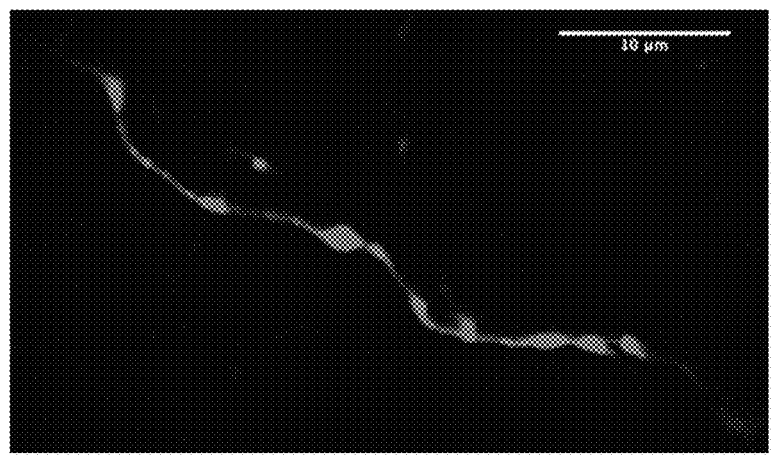
Figure 10E:
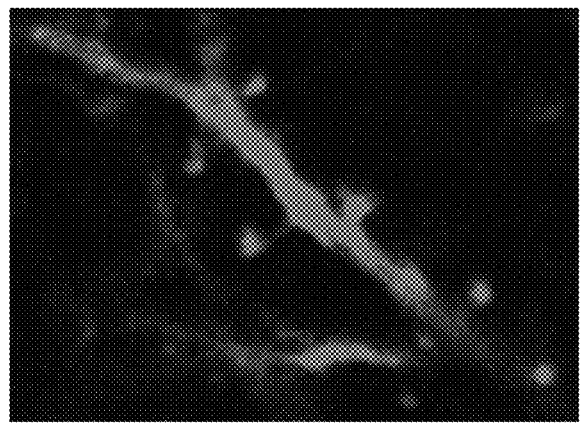
Figure 11A:
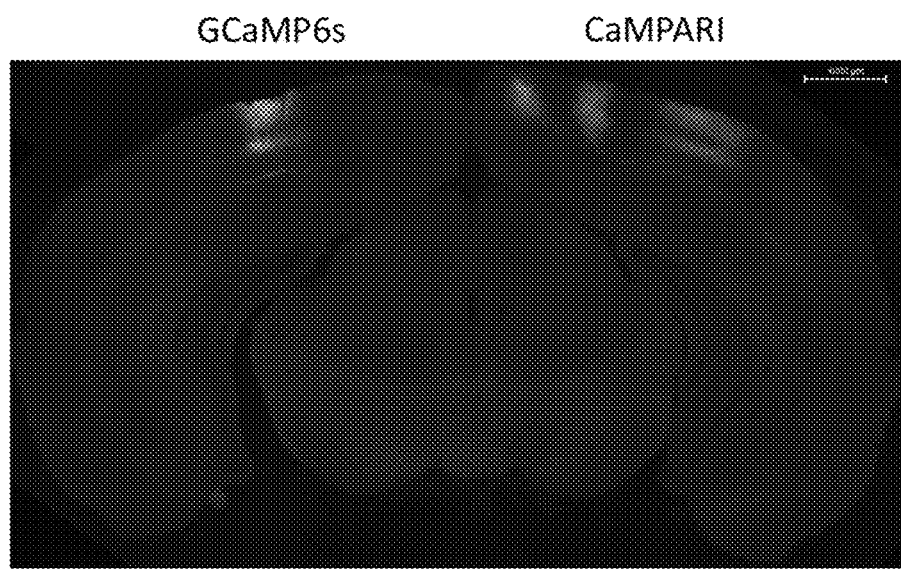
FIGS. 11A and 11B include images showing (A) a slide scanner image of green fluorescence from CaMPARI in a fixed 50 µM slice of mouse brain expressing CaMPARI from the human synapsin promoter three weeks after injection of adeno-associated virus (AAV), where three distinct AAV-CaMPARI injection sites are visible on the right side and one AAV-GCaMP injection site is visible on the left side for reference, and (B) a green fluorescence confocal microscopy image of the boxed region in (A) showing cell bodies of layer 2/3 (top right) and layer 5 (bottom left) cortical neurons.
Figure 11B:
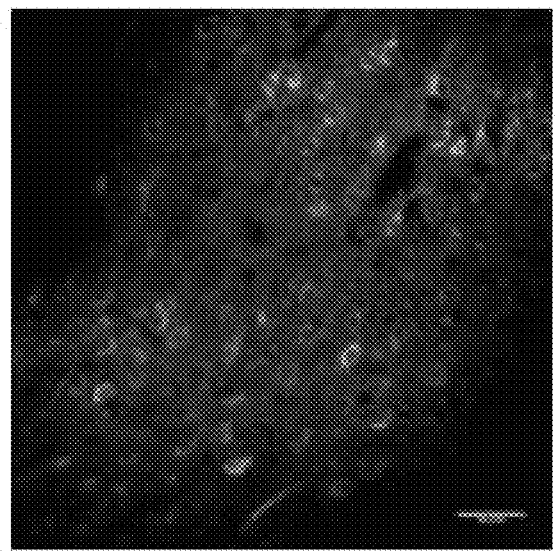

CaMPARI was expressed in cortical neurons of mouse brains after transgene delivery by either in utero electroporation (FIG. 10) or injection of AAV (FIG. 11). Green CaMPARI fluorescence was bright when imaging fixed sections using confocal microscopy. The fluorescence signal appeared evenly distributed throughout the cell bodies, with no punctuate labeling indicative of aggregation (FIGS. 10B, 10C, and 11B). Fine structures such as axonal boutons and dendritic spines were also visible (FIGS. 10D and 10E). Thus, CaMPARI served as a viable indicator after transgenic delivery.

Additionally, in another set of mice, 25 nL volumes of AAV 2/1 particles expressing CaMPARI from the human synapsin promoter (~1×10$^{13}$ genome copies per mL) in saline solution were stereotactically injected into the V1 region of visual cortex (injection site coordinates: 2.7 and 2.9 mm left and 0.2 mm anterior to Lambda suture) through the thinned skull of anesthetized C57BL/6J mice aged 1.5-2 months. 4-8 weeks after virus injection, a small craniotomy window was opened above the visual cortex and covered with a glass coverslip for imaging and photoconversion. In order to minimize undesirable CaMPARI photoconversion during cranial window implantation surgery, a 455 nm longpass filter (5CGA-455, Newport) was used with the illumination light source (Fiber-Lite). Mice were anesthetized using isoflurane (2.5% for induction, 1.5-2% during surgery). A circular craniotomy (2-2.5 mm diameter) was placed above V1 (centered 2.7 mm left, and 0.2 mm anterior to Lambda suture). The craniotomy was covered with 1% agarose, and a 3 mm round glass coverslip (no. 1 thickness, Warner Instruments) was cemented to the brain using black dental cement (Contemporary Ortho-Jet). A custom titanium head post was fixed to the skull using the same dental cement.

Mice were presented with moving grating stimuli using the Psychophysics Toolbox in MATLAB (Mathworks). Each stimulus trial consisted of a 4 s blank period (uniform gray display at mean luminance) followed by a 4 s drifting sinusoidal grating (0.05 cycles/degree, 1 Hz temporal frequency, 8 different directions). The visual stimuli were synchronized to individual image frames using frame-start pulses provided by ScanImage 4. The gratings were presented through an LCD monitor (30×40 cm), placed 25 cm in front of the center of the right eye (contralateral to the craniotomy window) of the mouse. The monitor subtended an angle of ±38° horizontally and ±31° vertically around the eye of the mouse.

First, green and red channel images of 4-8 fields of view (FOVs) were acquired within layer 2/3 of V1 (100-350 nm depth), as well as time-series data in the green channel during five consecutive displays of the drifting grating visual stimulus for each FOV. Next, the mouse was lowered from the objective lens and a custom-built connector was attached to its head to deliver photoconversion light, consisting of a bandpass filter (FF01-406/15, Semrock) and a lens (f=25 mm), coupled to an X-Cite exacte (Lumen Dynamics) light source with a liquid light guide. The connector focused photoconversion light onto a 5 mm-diameter area centered on the cranial window. 20×500 ms pulses of photoconversion light (900 mW/cm$^2$ at the cranial window) spaced 12 s apart were used. Each photoconversion light pulse was initiated 2 s into a 4 s display of moving gratings in one direction (northwest, 315°). After the photoconversion protocol was completed, the mouse was returned to its previous position under the objective lens, and the same FOVs imaged again. Correlation was observed between the responsive subset of cells before and after the photoconversion protocol, suggesting that the photoconversion did not cause substantial tissue damage.

Following the in vivo imaging, mice were euthanized and perfused with PBS followed by 4% PFA in PBS. Brain tissue was dissected out and post-fixed for 2 h in 4% PFA followed by soaking overnight in PBS with 10 mM EGTA. 100 μm sections were cut tangential to the in vivo imaging axis and floated on PBS with 10 mM EGTA prior to slide mounting with VECTASHIELD HardSet (Vector Laboratories). Mounted sections were imaged using a 20× objective on a confocal microscope.

All analyses were performed in MATLAB. ROIs corresponding to visually identifiable cell bodies were selected using a semi-automated algorithm. Ring shaped or circular ROIs were placed at the cytosolic regions of the cells (excluding the nucleus) or on its soma respectively. The fluorescence time course of each cell was measured by averaging all pixels within the ROI. The true fluorescence signal of a cell body was estimated as follows:

$$F_{cell\_true}(t) = F_{cell\_measured}(t) - r \cdot F_{neuropil}(t)$$

with r=0.7 throughout the study. Neuropil correction was applied only to cells with baseline fluorescence ($F_0$) signal stronger than their surrounding neuropil signal by more than 3%; other cells were excluded from the analysis. After neuropil correction, the $\Delta F/F_0$ and $F/F_0$ of each trial were calculated where $\Delta F = (F - F_0)$ and $F_0$ was averaged over a 2 s period immediately before the start of visual stimulation. Visually responsive neurons were defined as cells with $\Delta F/F_0 < -0.05$ (CaMPARI was a negative indicator) during at least one stimulus period, and using ANOVA across blank and eight direction periods (p<0.01); the same test was used to find neurons that were responsive to the stimulus shown during photoconversion. Cell were classified as responsive cells with significant response to the photoconversion stimulus (PC tuned), responsive cells without significant response to the photoconversion stimulus (responsive, not PC tuned), and non-responsive cells.

Figure 12A:
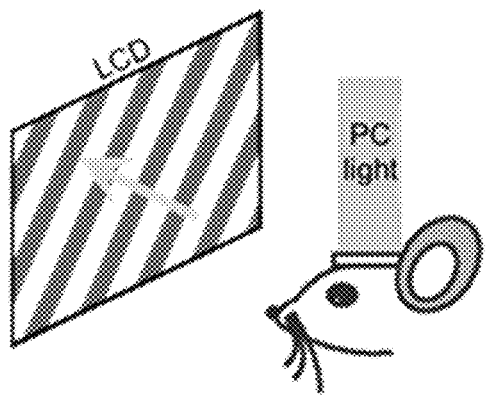
FIGS. 12A to 12F include results from a mouse primary visual cortex assay, showing (A) a schematic of the experimental setup, (B) a composite 2-photon image from cortical layer 2/3 of the primary visual cortex (V1) after visual stimulus and photoconversion (PC) light pulses. Two cells are circled. (C) calcium imaging fluorescence traces of two cells from layer 2/3 of V1 shown in (B) in response to different directions of drifting gratings, where an average baseline-normalized green CaMPARI fluorescence (F/F$_0$) from five trials is depicted as a trace, the leftmost vertical bar indicates the duration and direction of moving grating display during which PC light was pulsed, and the other vertical grey bars show the periods of visual stimulus that were not accompanied by PC light, (D) a plot of the CaMPARI red/green ratio of cells in layer 2/3 of V1 measured by calcium imaging response type (n=248; ***, P<0.001; n.s.=not significant, P=0.13; Mann-Whitney U tests), (E) a composite confocal image of fixed, sectioned tissue showing the same field of view as (B), and (F) a stitched composite confocal image of fixed, sectioned tissue (scale bars: 20 µm in (B) and (E), 200 µm in (F)).
Figure 12B:
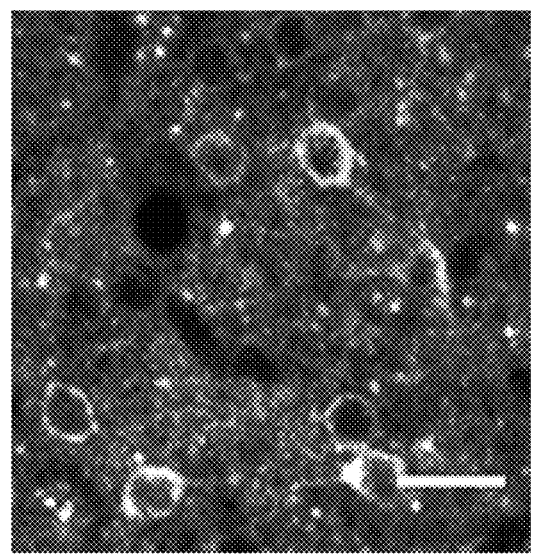
Figure 12C:
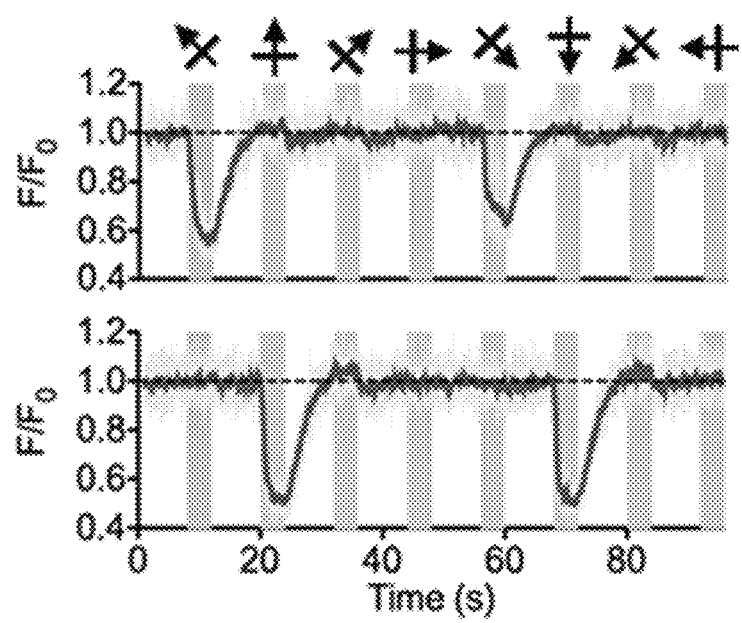
Figure 12D:
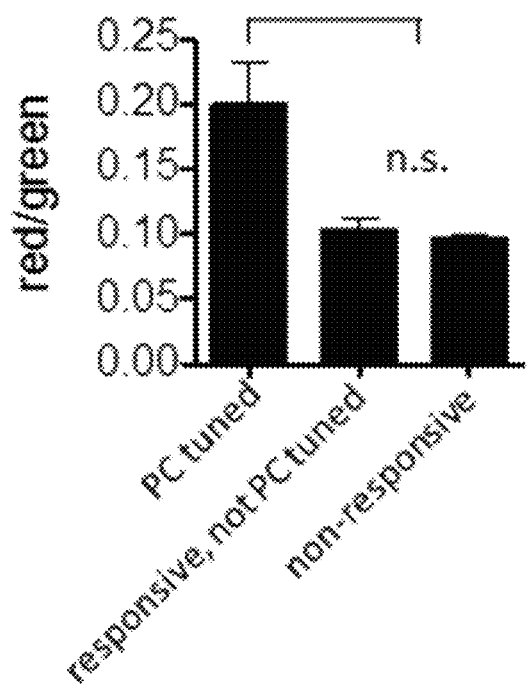

Within layer 2/3 of the mouse primary visual cortex (V1), neurons responding to different directions/orientations of moving bar gratings were interspersed throughout the tissue. CaMPARI expression was bright and nuclear-excluded (FIG. 12B). FIG. 12A shows in vivo calcium imaging was performed through the cranial window by exciting the CaMPARI green state with 2-photon light at 1000 nm as drifting gratings were presented. This allowed the generation of orientation-tuning maps of segmented cell bodies (FIG. 12C), the visual stimulus (a single direction—"northwest", preferred by cell 1 (FIG. 12C, top) but not cell 2 in (FIG. 12C, bottom)) was replayed, but instead of 2-photon imaging through an objective, bright 405 nm photoconversion light was delivered from a filtered metal halide lamp coupled through a liquid light guide and custom connector through the cranial window in 500 ms pulses. After 20 photoconversion pulses spaced 12 s apart, noticeable red fluorescence appeared in a subset of cells (cell 1, FIG. 12B) under 2-photon excitation. Neurons responsive to the "northwest" drifting grating displayed during photoconversion pulses exhibited a red/green ratio that was double the ratio of cells that were not responsive to that direction (FIG. 12D). Neurons that were responsive to some drifting grating directions, but not to "northwest", were less photoconverted and their red/green ratio resembled the population of cells that did not show a significant responses to any visual stimuli.

Figure 12E:
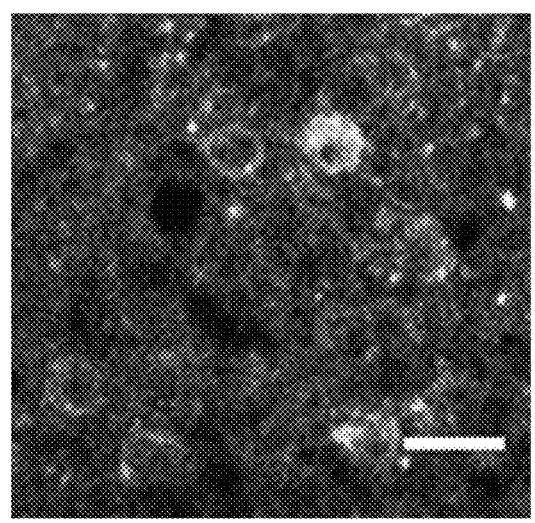
Figure 12F:
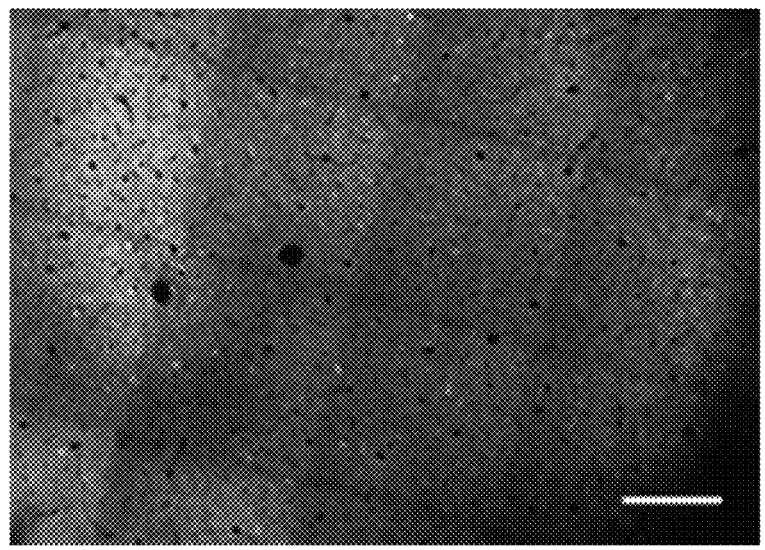

Both CaMPARI forms survived perfusion with 4% PFA primary fixative, vibratome sectioning and mounting for confocal microscopy (FIGS. 12E and 12F). Using vasculature and other landmarks, the FOVs were relocated from in vivo imaging (FIGS. 12B and 12E). The relative red/green ratio of cells was maintained following fixation, and the CaMPARI signal could be imaged over a much larger volume (FIG. 12F) than was easily accessible through the cranial window in vivo. When perfusion occurred 24 hours after photoconversion, marked cells could still be distinguished in fixed sections with confocal microscopy, showing that the CaMPARI photoconversion signal is stable over this time scale.

Example 7

This Example analyzes the ability of CaMPARI to track activity in genetically identified neurons that are inaccessible to conventional in vivo GECI imaging. For this Example, *Drosophila melanogaster* larvae were used as a test subject. Peripheral sensory neurons (PSNs) within the body wall of *Drosophila melanogaster* larvae control response to external stimuli such as touch (proprioceptive), vibration (chordotonal), and pain (nociceptive). Naturalistic behavioral responses to these stimuli include crawling and rolling, which prohibit restraint, and freely moving fly larvae are currently incompatible with functional imaging due to substantial movement artifacts.

Therefore, for this Example, embryos were collected and grown on larval fly food for four days at 25° C. and 65% humidity. Foraging third instar larvae were used for experiments. Before the experiments, the larvae were separated from food using 15% sucrose and washed with water. A single larva was then placed in the center of a 25×25 cm plastic plate containing 3% Bacto agar 2 cm above a 28 cm diameter amplified loudspeaker. The voltage input to the loudspeaker was used to modulate the amplitude of a 1000 Hz tone delivered to the agar plate, producing accelerations of the larvae in the range 0-3.7 m/s$^2$. PC light was delivered from a filtered metal halide lamp with a custom filter/lens housing (described for Example 6) positioned 5 cm directly above each larva to illuminate the whole animal. Each larva experienced one 5 s pulse of PC light and simultaneous 1000 Hz vibration stimulus (FIG. 13C). After delivering the stimulus and PC light, the larva CNS was dissected out and placed on a poly-lysine coated cover-slide in PBS with 10 mM EGTA. Confocal image stacks were acquired with a 710 laser-scanning confocal microscope (Zeiss) equipped with a 20× or 40× water-dipping objective.

Figure 13A:
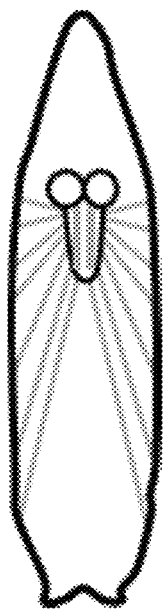
FIGS. 13A to 13E include results from freely moving subjects, showing (A) a schematic of labeled peripheral sensory neurons in a Drosophila larva, where cell bodies and dendrites are located along the body wall, and axons project to the brain (thin outline in center of larva) and branch along tracts within the ventral nerve cord (VNC), (B) confocal images of CaMPARI fluorescence in a subset of neurons in the VNC showing a z-projection of optical sections 20-30 µm below the dorsal surface of the VNC with rectangles and the letter 'P' indicating axonal projections of labeled proprioceptive neurons (left image) as well as a z-projection of optical sections 40-60 µm below the dorsal surface of the VNC with white and the letters 'C' and 'N' indicating axonal projections of labeled chordotonal and nociceptive neurons, respectively (right image) (scale bars=20 µm), (C) a schematic of an experimental setup having a freely crawling Drosophila larva on an agar plate pulsed with PC light from above while the larva is vibrated at 1000 Hz with a speaker from below, (D) a plot of the red/green CaMPARI fluorescence in various sensory neuron projections within the VNC measured from confocal microscopy stacks (**, P=0.003; n.s.=not significant, P>0.4; Student's t-tests), (E) a plot of dose response of red/green CaMPARI fluorescence in chordotonal axons within the VNC versus vibration amplitude, where lateral (closed circles) and ventral (open circles) axon tracts from chordotonal neurons were segmented and quantitated separately.
Figure 13B:
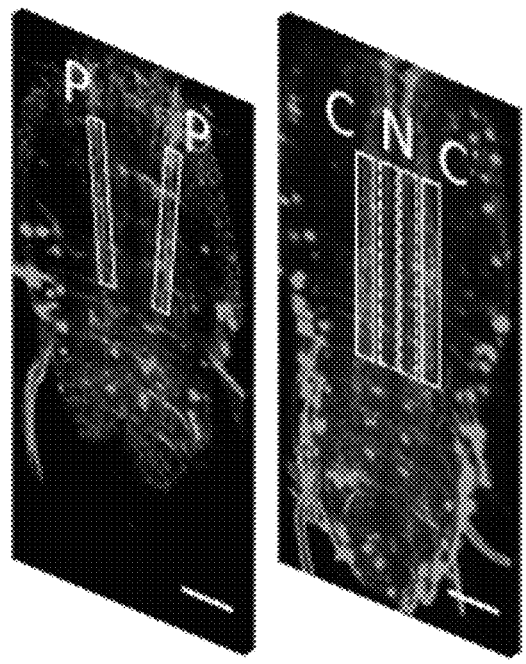
Figure 13C:
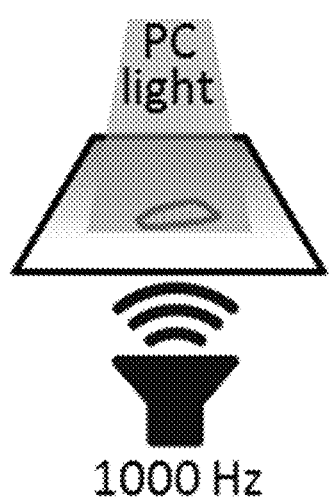
Figure 13D:
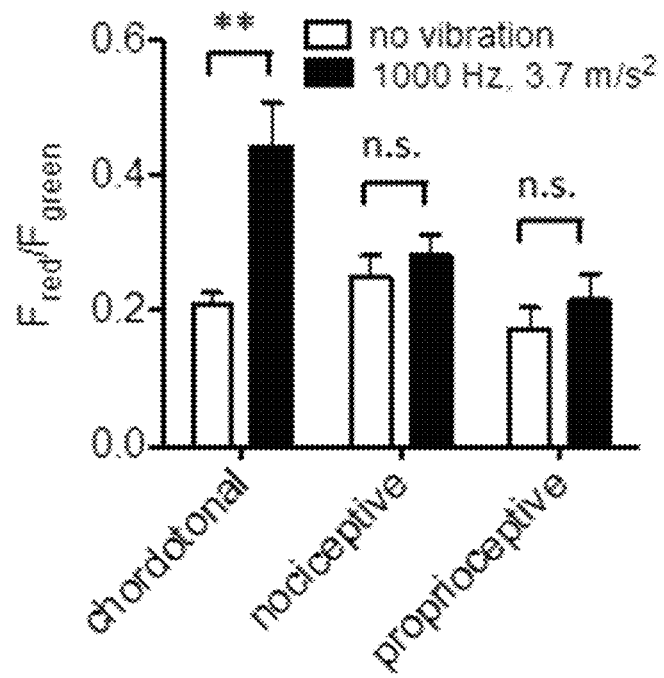
Figure 13E:
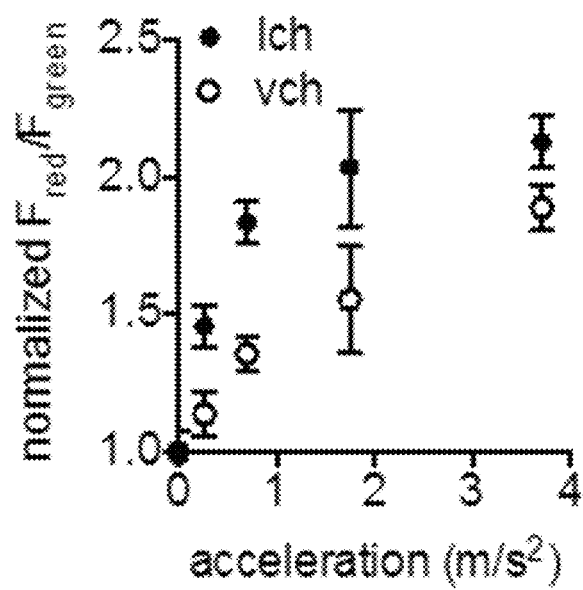

The P0163-GAL4 line drove CaMPARI expression in PSNs (FIGS. 13A and 13B). In third instar larvae, CaMPARI was clearly visible in PSN axonal projections in the ventral nerve cord (VNC), and could be segmented into proprioceptive, chordotonal, and nociceptive terminals based on known anatomy (FIG. 13B). Confocal imaging of dissected VNCs from these larvae showed that the vibration stimulus produced a significant increase in green-to-red photoconversion within the axonal projections of chordotonal neurons, and not the axons of proprioceptive or nociceptive neurons (FIG. 13D). Indeed, the extent of CaMPARI photoconversion within chordotonal axons increased in a dose-dependent manner with increasing amplitude of the vibration stimulus, with greater responses in lateral compared with ventral axons (FIG. 13E).

Figure 14A:
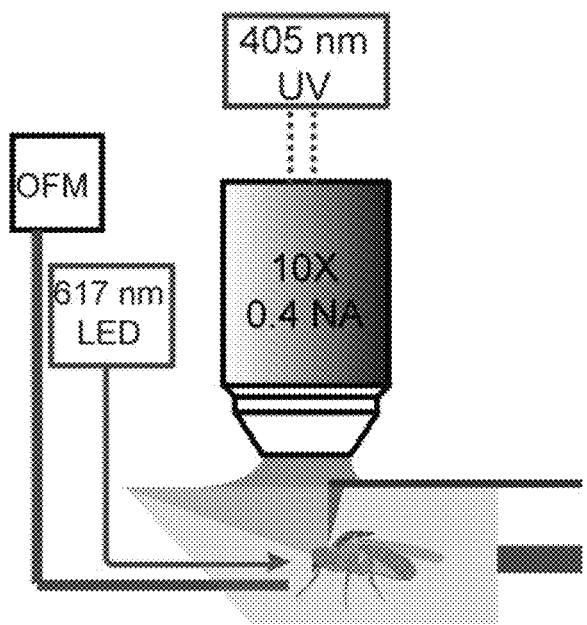
FIGS. 14A to 14L include results from functional mapping and circuit tracing in adult Drosophila, showing (A) a schematic of a setup for activity-driven CaMPARI labeling in the olfactory system of intact adult flies, (B) a schematic of olfactory circuitry, (C) odor-dependent response patterns of pan-neuronally expressed CaMPARI where, from left to right, there was no response to air, glomeruli (arrows) responded to 3-octanol (3-Oct), DA2 glomerulus (arrow) responded to geosmin (Geo), and VL2a (arrow) responded to phenylacetic acid (PAA), (D) a plot comprising glomeruli-specific responses to PAA in terms of the ratio between red and green channels at different photoconversion/stimulation durations (100 seconds, n=4; 200 seconds, n=4; 300 seconds, n=3), (E) ratiometric plots of the z-projection of all voxels of red-green ratios of representative glomeruli in (C), (F) maps of odor-response patterns in the antennal lobe (AL), (G) a response pattern in AL shown with MIP and Ir84a ORNs are co-labeled with mVenus, (H) a Z-projection of posterior sections showing activated projection neuron (PN) axons targeting mushroom body calyx via the mALT bundle and lateral horn through both mALT and mlALT bundles, (I) a Z-projection of additional medial sections showing that mlALT tract of PNs has been specifically labeled, (J) a Z-projection of posterior sections showing activated projection neuron (PN) axons targeting mushroom body calyx via the mALT bundle and lateral horn through both mALT and mlALT bundle, (K) a Z-projection of additional medial sections showing optogenetically activated primary (ORNs), secondary (PNs), and putatively tertiary neurons, and (L) activated quaternary descending neurons (DNs) projecting to VNC.
Figure 14B:
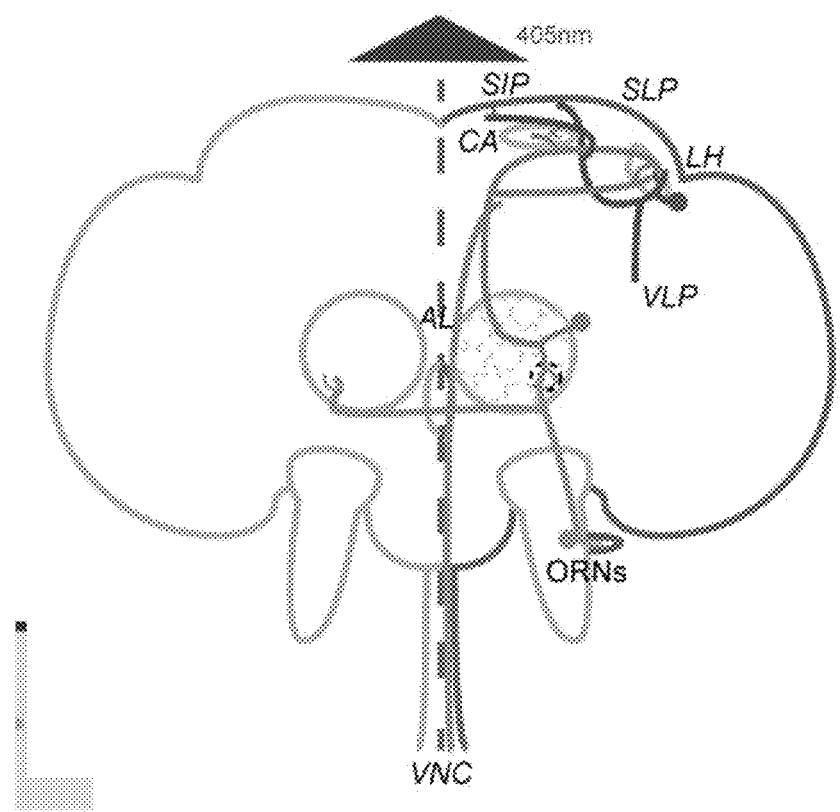

Additionally, in order to test whether CaMPARI could achieve trans-synaptic circuit tracing and whole-brain functional mapping, adult flies expressing CaMPARI were photo-converted pan-neuronally while activating sensory neurons. Intact flies were glued to a physiology holder and UV light was delivered through a water-dipping objective (FIG. 14A), thereby minimizing UV induced photo-damage while maximizing trans-cuticle photoconversion. The subjects were stimulated with a panel of odors, and the dissected brains were confocal-imaged immediately after odor exposure and photoconversion. Red/green ratios were used to identify, quantify, and compare odor responses in the brain (FIG. 14B). Three different odors were selected: (i), 3-octanol (3-Oct), an earthy odor known to activate multiple glomeruli in the first olfactory processing center in the fly brain, the antennal lobe (AL), (ii), geosmin (Geo), an odorant thought to alert flies to the presence of toxic microbes on yeast that has been described as specifically activating the DA2 glomerulus, and (iii), phenylacetic acid (PAA), a food-derived odor that promotes courtship in flies and strongly activates olfactory receptor neurons projecting to the VL2a glomerulus.

Figure 14C:
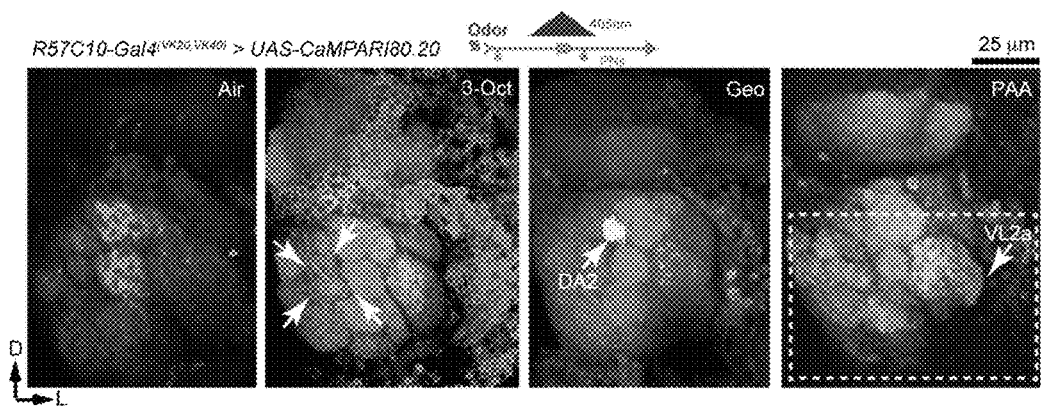
Figure 14D:
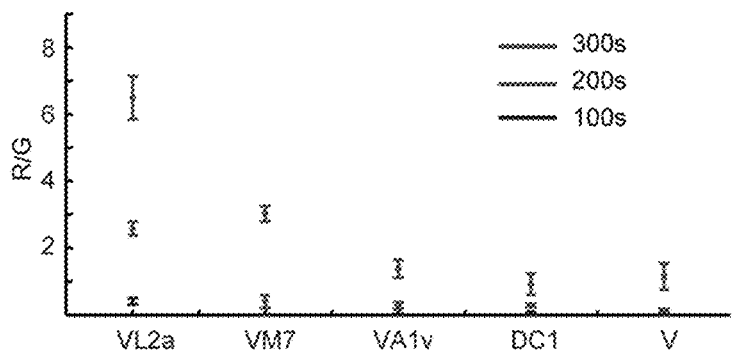
Figure 14E:
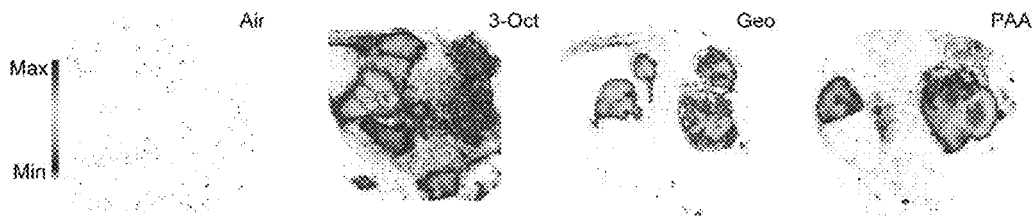
Figure 14F:
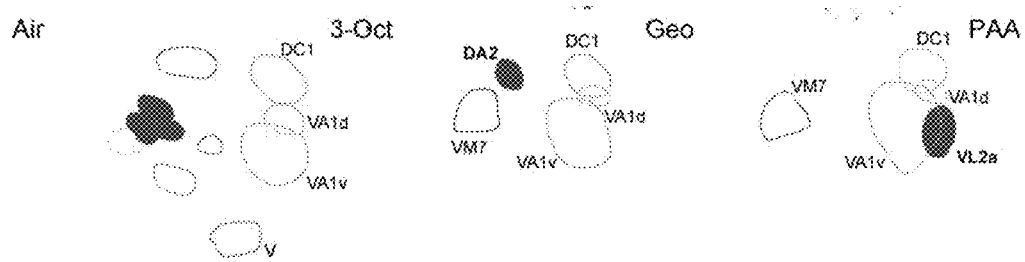

The results indicated that when CaMPARI was used to map the glomerular response pattern there was no response to air, 3-Oct activated many glomeruli, Geo activated mostly DA2, and PAA activated the VL2a glomerulus (FIG. 14C). Contrary to known techniques, additional glomeruli were also weakly co-activated (FIGS. 14E and 14F). In the case of PAA, this discrepancy may be explained by the fact that previously odor response was assessed using electrophysiology from specific Ir84a receptor neurons that project to a single glomerulus, rather than sampling the entire AL. For the Geo study, a specific driver, GH146-gal4, was used to drive GCaMP3. Expression heterogeneity could potentially account for the discrepancy. In support of this interpretation, when CaMPARI expression was driven with GH146-gal4, only the DA2 glomerulus was activated. The red/green ratio of different antennal lobe glomeruli in PAA-exposed flies was also quantified (FIG. 14D). VL2a was the most salient responder and VM7 was more weakly photo-converted. Increasing the integration time from 100 s to 300 s increased the overall red/green ratio without altering the relative amount of signal in different glomeruli (FIG. 14D). There was also evidence of projection neuron (PN) activation, and the activation of these secondary neurons was clear when the PN-specific GH146-gal4 was used. With GH146-gal4, photoconverted projections of PN axons were found to the mushroom body calyx (CA) and the lateral horn (LH), confirming that CaMPARI enabled trans-synaptic circuit mapping. The axons in LH arborized mostly in ventral LH, consistent with previous reports.

Figure 14G:
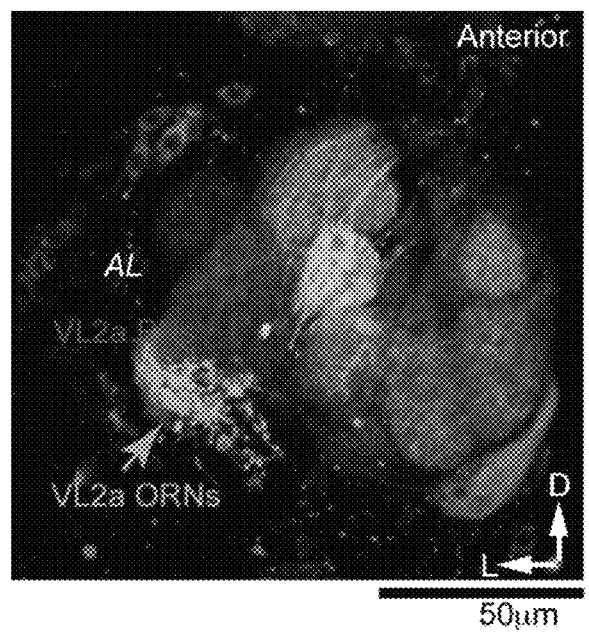
Figure 14H:
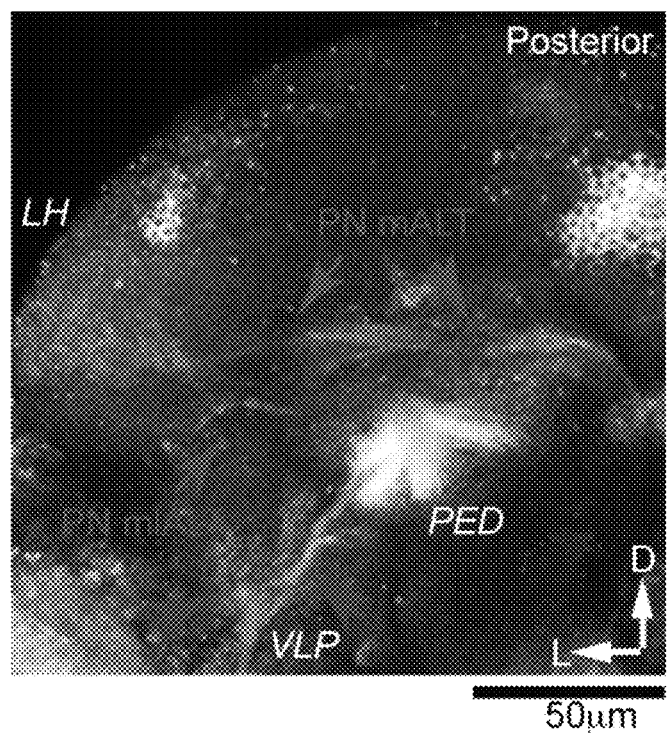
Figure 14I:
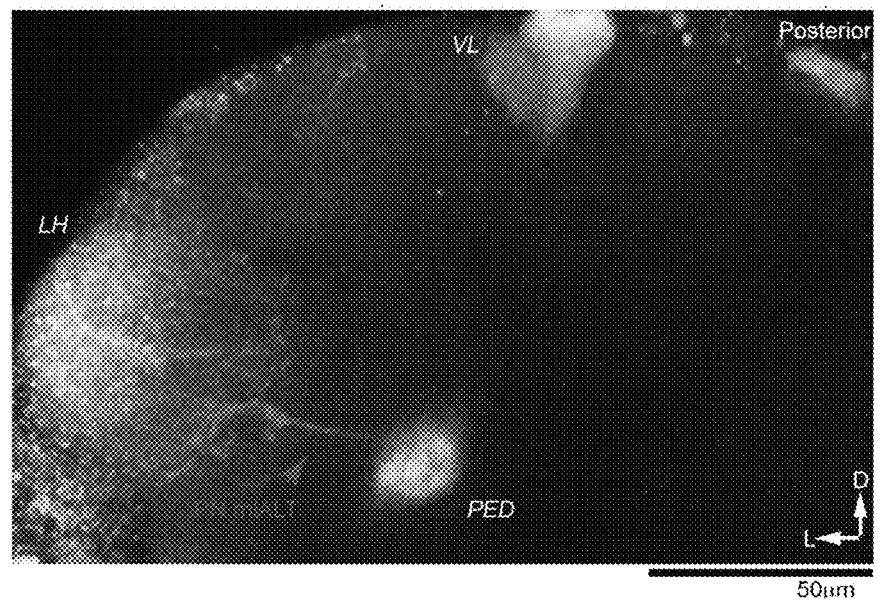
Figure 14J:
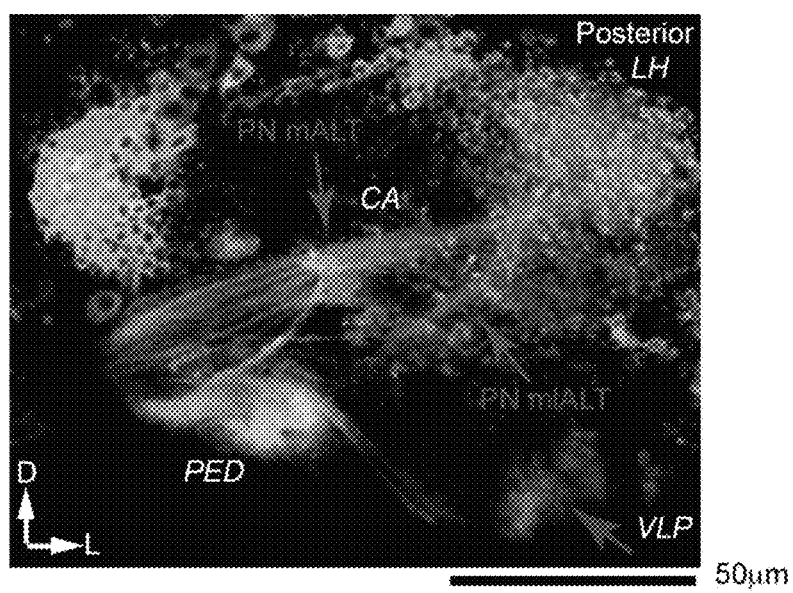
Figure 14K:
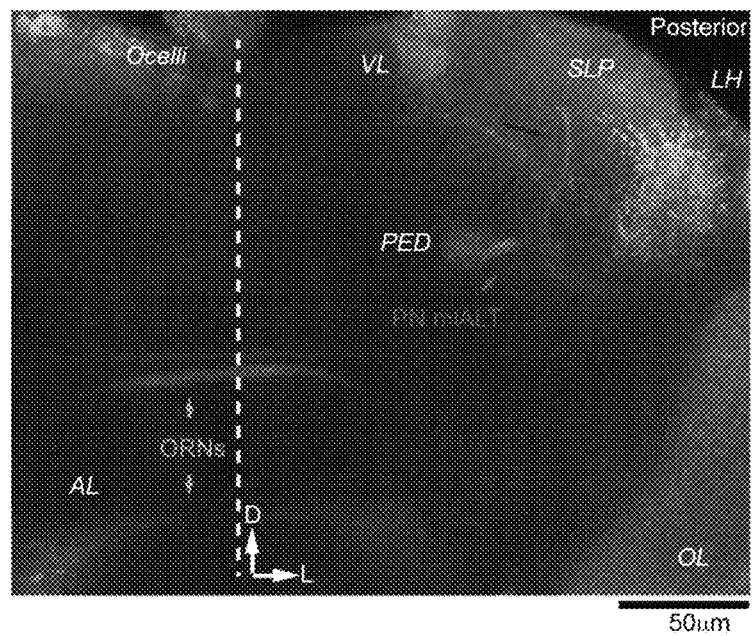
Figure 14L:
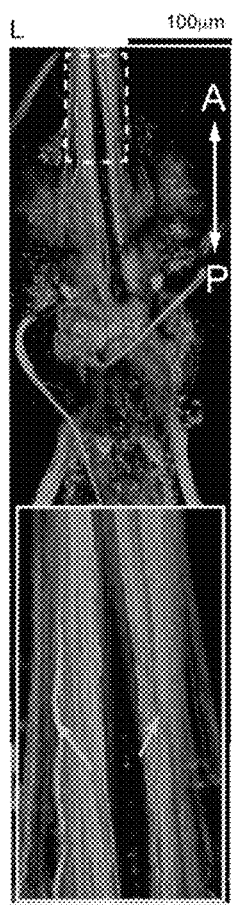

Next, it was determined whether sensory-driven circuit mapping with CaMPARI could also be complemented by the use of optogenetic stimulation to activate circuits downstream of an arbitrary cellular point of entry. Expression of the red light-drivable channel rhodopsin CsChrimson was driven in Ir84a receptor neurons using a LexA driver while expressing CaMPARI pan-neuronally with a R57C10-Gal4 driver. Circuits were then mapped throughout the brain during optogenetic stimulation of this single receptor neuron type. In addition to the glomeruli in the antennal lobe where axons of olfactory receptor neurons (ORNs) and dendrites of projection neurons (PNs) synapse (FIG. 14G), axons of PNs projected to the posterior areas of the brain (FIGS. 14H to 14K). One axon commissure, the medial antennal lobe tract (mALT), targeted both CA and LH (FIGS. 4H and 14I), while another commissure, the medial-lateral antennal lobe tract (mlALT), targeted LH directly. As with PAA odor-driven activation, photo-converted PN axons mostly target the ventral part of LH. In addition, potentially postsynaptic neurons of PNs, neurons in the mushroom body vertical lobe (VL, FIG. 14H) and VLP, were found to be activated (FIG. 14I). Using a high-affinity variant of CaMPARI, circuits that were further downstream were photo-converted (FIGS. 14J to 14L). Similar patterns of PNs and VLP neurons were found activated (FIG. 14J), as well as other tertiary cells such as LH neurons (FIG. 14K), mushroom body output neurons and some descending neuron projections (FIG. 14L). Activation of deeper layers of the circuit suggests that CsChrimson may be able to drive the firing rate of sensory neurons, and, as a consequence, downstream neurons, higher than natural stimulation does. On the other hand, known tools for functional mapping in *Drosophila* are much less sensitive than CaMPARI, and require hours of stimulation compared to several minutes for CaMPARI.

Example 8

This Example describes procedures conducted on zebrafish (*Danio rerio*) larvae. Larval zebrafish are an attractive neuroscience model due to their small size, rapid development and transparency. Whole-brain imaging with GECIs is possible, but requires restraint in agar and muscle paralysis, restricting the accessible range of behaviors and samples.

To demonstrate the utility of CaMPARI for whole-brain neural circuit marking during free behavior, stable transgenic zebrafish expressing CaMPARI in all neurons were generated from the elav/HuC promoter. Zebrafish were reared according to standard protocols and their developmental staging was reported in days post-fertilization (dpf), corresponding to staging at the standard temperature of 28.5° C. Embryos were either in casper or nacre background for their lack of pigmentation. Tg(elavl3:CaMPARI)$^{y/9}$ line was generated using the Tol2 transposition system, in which CaMPARI was subcloned into a Tol2 vector that contained a partial zebrafish elavl3 pan-neuronal promoter. The transgene construct and transposase RNA were injected into 1-4 cell-stage embryos and the transgenic lines were isolated by screening for expression of green fluorescence in the central nervous system in the F1 generation.

Larvae with bright green fluorescence in the central nervous system were used at 4-5 days post-fertilization (dpf). Fish were placed individually into 6 cm plastic dishes containing system water under a 405 nm light-emitting diode (LED) array (Loctite) for photoconversion. The LED array had an intensity of 400 mW/cm$^2$ at the fish, evenly illuminated the entire dish, was triggered using a foot pedal switch, and had an internal timer for precise timing of light exposure. Fish were exposed to one pulse of 10 s of photoconversion light under various conditions, then embedded in 2% agarose in system water with 0.24 mg/mL tricaine methanesulfonate (MS-222, Sigma) for confocal imaging (Zeiss 710). Z-stacks (2 μm step) were acquired using a 20× water-dipping objective between the dorsal and ventral brain surfaces in a 1×2 tiled array to visualize all of the central brain and a portion of the spinal cord.

When the green CaMPARI fluorescence was imaged using only the 488 nm laser line, a rapid decrease in the green fluorescence intensity was observed as a function of sample depth. We therefore imaged the green CaMPARI fluorescence using both the 488 nm and 405 nm laser lines, and the 405 nm laser line was included to photoswitch the green CaMPARI fluorescence to the brighter state for imaging. The red CaMPARI fluorescence was imaged using both the 561 nm and 440 nm lines.

Figure 15:
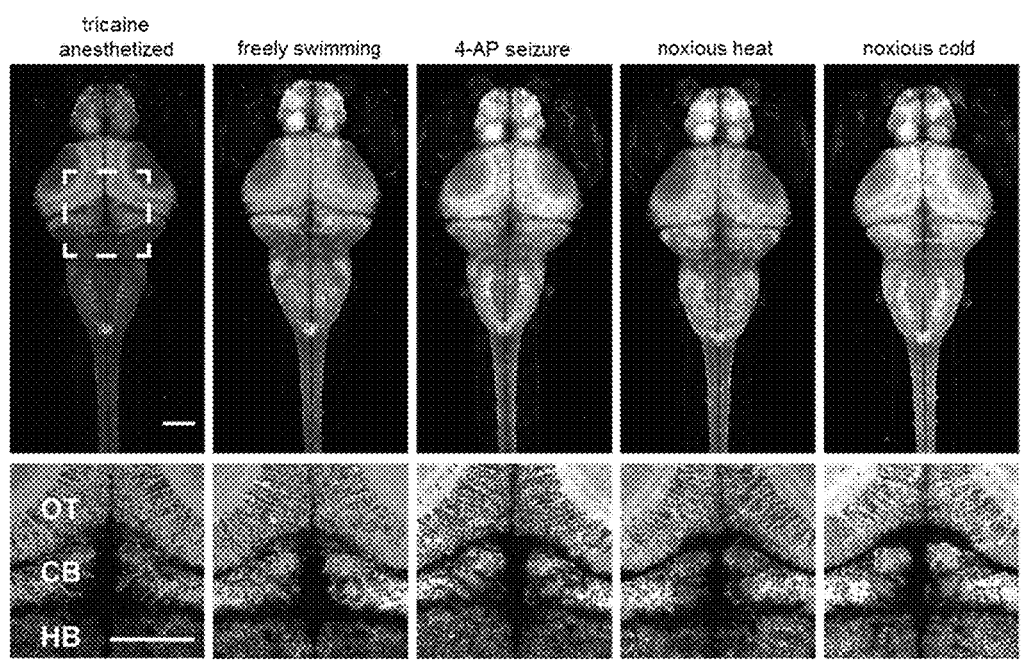
FIG. 15 includes confocal images showing zebrafish larvae 4 days post-fertilization and following 10 s of photoconversion light, applied during exposure to different neuroactive compounds or stimuli, where the top panels are maximum-intensity Z-projections of the entire zebrafish brain, and the bottom panels are individual Z-slices from the same fish.

The confocal stacks that were acquired generated a cellular-resolution snapshot of the calcium state of all neurons in the zebrafish brain (FIG. 15). A consistent pattern of photoconverted neurons was repeatedly observed when fish were photoconverted while freely swimming in the absence of external stimuli. Exposure of larvae anesthetized with tricaine methanesulfonate (MS-222, sodium channel blocker) to 405-nm light resulted in a complete lack of photoconversion across the brain. Treatment of larvae with pro-convulsive compounds or exposure to noxious heat or cold stimuli during the photoconversion light pulse resulted in qualitatively different patterns of CaMPARI photoconversion throughout the brain, consistent with permanent marking of the subset of neurons activated by each of these stimuli. CaMPARI signal following each stimulus was consistent between fish and showed clear cellular resolution (FIG. 15, bottom panels).

It will be understood that various details of the presently disclosed subject matter can be changed without departing from the scope of the subject matter disclosed herein. Furthermore, the description provided herein is for the purpose of illustration only, and not for the purpose of limitation.

While the terms used herein are believed to be well understood by one of ordinary skill in the art, definitions are set forth herein to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are described herein.

The terms "comprising", "including," and "having" are intended to be inclusive and mean that there may be additional elements other than the listed elements.

Following long-standing patent law convention, the terms "a", "an", and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Various abbreviations used are used herein, and the following is a list of some of these abbreviations and their corresponding meanings: ORN: olfactory-receptor neurons; PN: projection neurons; mALT: medial antennal lobe tract; mlALT: mediolateral antennal lobe tract; AL: antennal lobe; LH: lateral horn; CA: mushroom body calyx; PED: peduncules; SLP: superior lateral protocerebrum; SIP: superior lateral protocerebrum; VNC: ventral nerve cord; VL: vertical lobe; OL: optic lobe; AOTU: Anterior optic tubercles; AMMC: antennal mechanosensory and motor center.

Throughout this document, various references are mentioned, including various publications, patents, and patent applications. All such references are incorporated herein by reference, including the references set forth in the following list:

REFERENCES

1. P. F. Baker, A. L. Hodgkin, E. B. Ridgway, Depolarization and calcium entry in squid giant axons. *J Physiol* 218, 709-755 (1971).
2. D. W. Tank, M. Sugimori, J. A. Connor, R. R. Llinas, Spatially resolved calcium dynamics of mammalian Purkinje cells in cerebellar slice. *Science* 242, 773-777 (1988).
3. J. L. Chen, M. L. Andermann, T. Keck, N. L. Xu, Y. Ziv, Imaging neuronal populations in behaving rodents: paradigms for studying neural circuits underlying behavior in the mammalian cortex. *J Neurosci* 33, 17631-17640 (2013).
4. T. Riemensperger, U. Pech, S. Dipt, A. Fiala, Optical calcium imaging in the nervous system of *Drosophila melanogaster*. *Biochimica et biophysica acta* 1820, 1169-1178 (2012).
5. L. Tian, S. A. Hires, L. L. Looger, Imaging neuronal activity with genetically encoded calcium indicators. *Cold Spring Harbor protocols* 2012, 647-656 (2012).
6. E. Dreosti, B. Odermatt, M. M. Dorostkar, L. Lagnado, A genetically encoded reporter of synaptic activity in vivo. *Nat Methods* 6, 883-889 (2009).
7. J. F. Guzowski, J. A. Timlin, B. Roysam, B. L. McNaughton, P. F. Worley, C. A. Barnes, Mapping behaviorally relevant neural circuits with immediate-early gene expression. *Current opinion in neurobiology* 15, 599-606 (2005).
8. S. Ramirez, X. Liu, P. A. Lin, J. Suh, M. Pignatelli, R. L. Redondo, T. J. Ryan, S. Tonegawa, Creating a false memory in the hippocampus. *Science* 341, 387-391 (2013).
9. R. Y. Tsien, Very long-term memories may be stored in the pattern of holes in the perineuronal net. *Proc Natl Acad Sci USA* 110, 12456-12461 (2013).
10. D. H. O'Connor, D. Huber, K. Svoboda, Reverse engineering the mouse brain. *Nature* 461, 923-929 (2009).
11. T. W. Chen, T. J. Wardill, Y. Sun, S. R. Pulver, S. L. Renninger, A. Baohan, E. R. Schreiter, R. A. Kerr, M. B. Orger, V. Jayaraman, L. L. Looger, K. Svoboda, D. S. Kim, Ultrasensitive fluorescent proteins for imaging neuronal activity. *Nature* 499, 295-300 (2013).
12. J. Akerboom, J. D. Rivera, M. M. Guilbe, E. C. Malave, H. H. Hernandez, L. Tian, S. A. Hires, J. S. Marvin, L. L. Looger, E. R. Schreiter, Crystal structures of the GCaMP calcium sensor reveal the mechanism of fluorescence signal change and aid rational design. *J Biol Chem* 284, 6455-6464 (2009).
13. J. Wiedenmann, S. Ivanchenko, F. Oswald, F. Schmitt, C. Rocker, A. Salih, K. D. Spindler, G. U. Nienhaus, EosFP, a fluorescent marker protein with UV-inducible green-to-red fluorescence conversion. *Proc Natl Acad Sci USA* 101, 15905-15910 (2004).
14. H. Hoi, T. Matsuda, T. Nagai, R. E. Campbell, Highlightable Ca2+ indicators for live cell imaging. *Journal of the American Chemical Society* 135, 46-49 (2013).
15. C. M. Niell, M. P. Stryker, Highly selective receptive fields in mouse visual cortex. *J Neurosci* 28, 7520-7536 (2008).
16. M. B. Ahrens, M. B. Orger, D. N. Robson, J. M. Li, P. J. Keller, Whole-brain functional imaging at cellular resolution using light-sheet microscopy. *Nat Methods* 10, 413-420 (2013).
17. T. Hummel, K. Krukkert, J. Roos, G. Davis, C. Klambt, *Drosophila* Futsch/22C10 is a MAP1B-like protein required for dendritic and axonal development. *Neuron* 26, 357-370 (2000).
18. T. Ohyama, T. Jovanic, G. Denisov, T. C. Dang, D. Hoffmann, R. A. Kerr, M. Zlatic, High-throughput analysis of stimulus-evoked behaviors in *Drosophila* larva reveals multiple modality-specific escape strategies. *PLoS One* 8, e71706 (2013).
19. M. C. Stensmyr, H. K. Dweck, A. Farhan, I. Ibba, A. Strutz, L. Mukunda, J. Linz, V. Grabe, K. Steck, S. Lavista-Llanos, D. Wicher, S. Sachse, M. Knaden, P. G. Becher, Y. Seki, B. S. Hansson, A conserved dedicated olfactory circuit for detecting harmful microbes in *Drosophila*. *Cell* 151, 1345-1357 (2012).
20. Y. Grosjean, R. Rytz, J. P. Farine, L. Abuin, J. Cortot, G. S. Jefferis, R. Benton, An olfactory receptor for food-derived odours promotes male courtship in *Drosophila*. *Nature* 478, 236-240 (2011).
21. N.C. Klapoetke, Y. Murata, S. S. Kim, S. R. Pulver, A. Birdsey-Benson, Y. K. Cho, T. K. Morimoto, A. S. Chuong, E. J. Carpenter, Z. Tian, J. Wang, Y. Xie, Z. Yan, Y. Zhang, B. Y. Chow, B. Surek, M. Melkonian, V. Jayaraman, M. Constantine-Paton, G. K. Wong, E. S. Boyden, Independent optical excitation of distinct neural populations. *Nat Methods* 11, 338-346 (2014).
22. J. S. Marvin, B. G. Borghuis, L. Tian, J. Cichon, M. T. Harnett, J. Akerboom, A. Gordus, S. L. Renninger, T. W. Chen, C. I. Bargmann, M. B. Orger, E. R. Schreiter, J. B. Demb, W. B. Gan, S. A. Hires, L. L. Looger, An optimized fluorescent probe for visualizing glutamate neurotransmission. *Nat Methods* 10, 162-170 (2013).
23. J. S. Marvin, E. R. Schreiter, I. M. Echevarria, L. L. Looger, A genetically encoded, high-signal-to-noise maltose sensor. *Proteins* 79, 3025-3036 (2011).
24. I. Alicea, J. S. Marvin, A. E. Miklos, A. D. Ellington, L. L. Looger, E. R. Schreiter, Structure of the *Escherichia coli* phosphonate binding protein PhnD and rationally optimized phosphonate biosensors. *Journal of molecular biology* 414, 356-369 (2011).
25. V. Venkatachalam, D. Brinks, D. Maclaurin, D. Hochbaum, J. Kralj, A. E. Cohen, Flash memory: photochemical imprinting of neuronal action potentials onto a microbial rhodopsin. *Journal of the American Chemical Society* 136, 2529-2537 (2014).
26. Ando, R., Hama, H., Yamamoto-Hino, M., Mizuno, H. & Miyawaki, A. An optical marker based on the UV-induced green-to-red photoconversion of a fluorescent protein. *Proc Natl Acad Sci USA* 99, 12651-12656 (2002).
27. Baird, G. S., Zacharias, D. A. & Tsien, R. Y. Circular permutation and receptor insertion within green fluorescent proteins. *Proc Natl Acad Sci USA* 96, 11241-11246 (1999).
28. McKinney, S. A., Murphy, C. S., Hazelwood, K. L., Davidson, M. W. & Looger, L. L. A bright and photostable photoconvertible fluorescent protein. *Nat Methods* 6, 131-133 (2009).
29. Akerboom, J., Chen, T. W., Wardill, T. J., Tian, L., Marvin, J. S. et al. Optimization of a GCaMP calcium indicator for neural activity imaging. *J Neurosci* 32, 13819-13840 (2012).

30. Thorn, P. Ca2+ influx during agonist and Ins(2,4,5)P3-evoked Ca2+ oscillations in HeLa epithelial cells. *J Physiol* 482 (Pt 2), 275-281 (1995).
31. F. W. Studier, Protein production by auto-induction in high density shaking cultures. *Protein Expr Purif* 41, 207-234 (2005).
32. T. G. Battye, L. Kontogiannis, O. Johnson, H. R. Powell, A. G. Leslie, iMOSFLM: a new graphical interface for diffraction-image processing with MOSFLM. *Acta Crystallogr D Biol Crystallogr* 67, 271-281 (2011).
33. A. G. W. Leslie, in *Joint CCP4+ESF-EAMCB Newsletter on Protein Crystallography*. (1992), vol. 26.
34. M. D. Winn, C. C. Ballard, K. D. Cowtan, E. J. Dodson, P. Emsley, P. R. Evans, R. M. Keegan, E. B. Krissinel, A. G. Leslie, A. McCoy, S. J. McNicholas, G. N. Murshudov, N. S. Pannu, E. A. Potterton, H. R. Powell, R. J. Read, A. Vagin, K. S. Wilson, Overview of the CCP4 suite and current developments. *Acta Crystallogr D Biol Crystallogr* 67, 235-242 (2011).
35. A. J. McCoy, R. W. Grosse-Kunstleve, P. D. Adams, M. D. Winn, L. C. Storoni, R. J. Read, Phaser crystallographic software. *J Appl Crystallogr* 40, 658-674 (2007).
36. K. Nienhaus, G. U. Nienhaus, J. Wiedenmann, H. Nar, Structural basis for photo-induced protein cleavage and green-to-red conversion of fluorescent protein EosFP. *Proc Natl Acad Sci USA* 102, 9156-9159 (2005).
37. P. Emsley, B. Lohkamp, W. G. Scott, K. Cowtan, Features and development of Coot. *Acta Crystallogr D Biol Crystallogr* 66, 486-501 (2010).
38. T. J. Wardill, T. W. Chen, E. R. Schreiter, J. P. Hasseman, G. Tsegaye, B. F. Fosque, R. Behnam, B. C. Shields, M. Ramirez, B. E. Kimmel, R. A. Kerr, V. Jayaraman, L. L. Looger, K. Svoboda, D. S. Kim, A neuron-based screening platform for optimizing genetically-encoded calcium indicators. *PLoS One* 8, e77728 (2013).
39. T. A. Pologruto, B. L. Sabatini, K. Svoboda, ScanImage: flexible software for operating laser scanning microscopes. *Biomed Eng Online* 2, 13 (2003).
40. D. H. Brainard, The psychophysics toolbox. *Spatial vision* 10, 433-436 (1997).
41. D. G. Pelli, The VideoToolbox software for visual psychophysics: Transforming numbers into movies. *Spatial vision* 10, 437-442 (1997).
42. A. M. Kerlin, M. L. Andermann, V. K. Berezovskii, R. C. Reid, Broadly tuned response properties of diverse inhibitory neuron subtypes in mouse visual cortex. *Neuron* 67, 858-871 (2010).
43. K. Ohki, S. Chung, Y. H. Ch'ng, P. Kara, R. C. Reid, Functional imaging with cellular resolution reveals precise micro-architecture in visual cortex. *Nature* 433, 597-603 (2005).
44. M. Westerfield, *The zebrafish book: a guide for the laboratory use of zebrafish (Brachydanio rerio)*. (M. Westerfield, Eugene, Oreg., 1993).
45. J. A. Lister, C. P. Robertson, T. Lepage, S. L. Johnson, D. W. Raible, nacre encodes a zebrafish microphthalmia-related protein that regulates neural-crest-derived pigment cell fate. *Development* 126, 3757-3767 (1999).
46. R. M. White, A. Sessa, C. Burke, T. Bowman, J. LeBlanc, C. Ceol, C. Bourque, M. Dovey, W. Goessling, C. E. Burns, L. I. Zon, Transparent adult zebrafish as a tool for in vivo transplantation analysis. *Cell stem cell* 2, 183-189 (2008).
47. A. Urasaki, G. Morvan, K. Kawakami, Functional dissection of the Tol2 transposable element identified the minimal cis-sequence and a highly repetitive sequence in the subterminal region essential for transposition. *Genetics* 174, 639-649 (2006).
48. T. Sato, M. Takahoko, H. Okamoto, HuC:Kaede, a useful tool to label neural morphologies in networks in vivo. *Genesis* 44, 136-142 (2006).
49. S. Fisher, E. A. Orrice, R. M. Vinton, S. L. Bessling, A. Urasaki, K. Kawakami, A. S. McCallion, Evaluating the biological relevance of putative enhancers using Tol2 transposon-mediated transgenesis in zebrafish. *Nature protocols* 1, 1297-1305 (2006).

What is claimed is:

1. An isolated polypeptide, comprising: an EosFP polypeptide, which includes
    a C-terminus portion comprising the amino acid sequence of SEQ ID NO. 2, a variant thereof having 95% identity to SEQ ID NO. 2, or a fragment thereof wherein 1-5 amino acids removed relative to SEQ ID NO. 2, and
    an N-terminus portion comprising the amino acid sequence of SEQ ID NO. 3, a variant thereof having 95% identity to SEQ ID NO. 3, or a fragment thereof wherein 1-5 amino acids removed relative to SEQ ID NO. 3;
    a calmodulin (CaM) polypeptide, comprising the amino acid sequence of SEQ ID NO. 4, a variant thereof having 95% identity to SEQ ID NO. 4, or a fragment thereof wherein 1-5 amino acids removed relative to SEQ ID NO. 4; and
    a M13 polypeptide, comprising the amino acid sequence of SEQ ID NO. 5, a variant thereof having mutations at residues of position 2, 6, 9, 10, 11, and/or 13 of SEQ ID NO: 5, or a fragment thereof wherein 1-5 amino acids removed relative to SEQ ID NO. 5.

2. The isolated polypeptide of claim 1, wherein the isolated polypeptide comprises the amino acid sequence of SEQ ID NO. 1.

3. The isolated polypeptide of claim 1, wherein, from an N-terminus to a C-terminus, the isolated polypeptide comprises the CaM polypeptide, the EosFP polypeptide, and the M13 polypeptide.

4. The isolated polypeptide of claim 1, wherein, from a C-terminus to an N-terminus, the isolated polypeptide comprises the CaM polypeptide, the EosFP polypeptide, and the M13 polypeptide.

5. The isolated polypeptide of claim 1, further comprising a first polypeptide linker disposed between the CaM polypeptide and the EosFP polypeptide, a second polypeptide linker disposed between the EosFP polypeptide and the M13 polypeptide, an inter-domain linker disposed between the C-terminus portion of the EosFP polypeptide and the N-terminus portion of the EosFP polypeptide, or a combination thereof.

6. The isolated polypeptide of claim 5, wherein the inter-domain linker comprises about 1 to about 6 amino acids.

7. The isolated polypeptide of claim 5, wherein the inter-domain linker comprises an amino acid sequence of SEQ ID NO. 13.

8. The isolated polypeptide of claim 5, wherein the first polypeptide linker includes a 6×His tag.

9. The isolated polypeptide of claim 1, further comprising a nuclear export signal (NES).

10. The isolated polypeptide of claim 9, wherein the NES is at a N-terminus of the isolated polypeptide and/or at a C-terminus of the isolated polypeptide.

11. The isolated polypeptide of claim 9, wherein the NES comprises the sequence of SEQ ID NO: 6.

12. The isolated polypeptide of claim 1, wherein the M13 polypeptide comprises a variant of the amino acid sequence of SEQ ID NO. 5, wherein the mutations of the variant are selected from the group consisting of S2L, W6Y, W6L, W6V, W6M, W6H, W6F, T9A, T9D, G10D, G10A, H11K, V13H, V13S, V13T, V13A, V13D, and V13L.

13. The isolated polypeptide of claim 1, wherein the isolated polypeptide comprises a variant of the amino acid sequence of SEQ ID NO. 1, wherein mutations of the variant are selected from the group consisting of Q171V, Q171T, Q171R, M172R, M172L, M173T, A175L, H194W, F227Y, C231R, C231T, C231A, I232V, I232C, L246I, L281V, N374A, and N374S.

14. The isolated polypeptide of claim 1, wherein the EosFP polypeptide includes a circular permutation on a beta strand of the EosFP polypeptide selected from the beta strand 1, 5, 7, 8, 9, and combinations thereof.

15. The isolated polypeptide of claim 1, wherein, in the presence of calcium, a fluorescence emitted by the isolated polypeptide shifts from green to red.

16. The isolated polypeptide of claim 1, wherein the EosFP polypeptide includes a C-terminus portion comprising the amino acid sequence of SEQ ID NO. 2 and a N-terminus portion comprising the amino acid sequence of SEQ ID NO. 3; the calmodulin (CaM) polypeptide comprises the amino acid sequence of SEQ ID NO. 4; and the M13 polypeptide comprises the amino acid sequence of SEQ ID NO. 5.

17. The isolated polypeptide of claim 1, wherein
    the EosFP polypeptide comprises
        a C-terminus portion comprising a fragment of the amino acid sequence of SEQ ID NO. 2, wherein the fragment has the amino acid sequence of SEQ ID NO: 2 wherein 1-5 amino acids are removed relative to SEQ ID NO. 2 and
        a N-terminus portion comprising a fragment of the amino acid sequence of SEQ ID NO. 3, wherein the fragment has the amino acid sequence of SEQ ID NO: 3 wherein 1-5 amino acids are removed relative to SEQ ID NO. 3;
    the calmodulin (CaM) polypeptide comprises a fragment of the amino acid sequence of SEQ ID NO. 4, wherein the fragment has the amino acid sequence of SEQ ID NO: 4 wherein 1-5 amino acids are removed relative to SEQ ID NO. 4; and
    the M13 polypeptide comprises a fragment of the amino acid sequence of SEQ ID NO. 5, wherein the fragment has the amino acid sequence of SEQ ID NO: 5 wherein 1-5 amino acids are removed relative to SEQ ID NO. 5.

18. The isolated polypeptide of claim 1, wherein the isolated polypeptide comprises the amino acid sequence of SEQ ID NO. 8, SEQ ID NO. 10, or SEQ ID NO. 12.

19. The isolated polypeptide of claim 1, wherein
    the EosFP polypeptide comprises
        a C-terminus portion comprising a variant of the amino acid sequence of SEQ ID NO. 2, having at least 98% identity to SEQ ID NO. 2 and
        a N-terminus portion comprising a variant of the amino acid sequence of SEQ ID NO. 3, having at least 98% identity to SEQ ID NO. 3;
    the calmodulin (CaM) polypeptide comprises a variant of the amino acid sequence of SEQ ID NO. 4, having at least 98% identity to SEQ ID NO. 4; and
    the M13 polypeptide comprises a variant of the amino acid sequence of SEQ ID NO. 5, having at least 98% identity to SEQ ID NO. 5.

20. The isolated polypeptide of claim 1, wherein the EosFP polypeptide includes a C-terminus portion comprising the amino acid sequence of SEQ ID NO. 2 and a N-terminus portion comprising the amino acid sequence of SEQ ID NO. 3; the calmodulin (CaM) polypeptide comprises the amino acid sequence of SEQ ID NO. 4; and the M13 polypeptide comprises a variant of the amino acid sequence of SEQ ID NO. 5, wherein mutations of the variant are selected from the group consisting of S2L, W6Y, W6L, W6V, W6M, W6H, W6F, T9A, T9D, G10D, G10A, H11K, V13H, V13S, V13T, V13A, V13D, V13L.

21. The isolated polypeptide of claim 1, wherein the isolated polypeptide comprises a variant of the amino acid sequence of SEQ ID NO. 1, having 95% identity to SEQ ID NO: 1.

* * * * *